(12) United States Patent
Priepke et al.

(10) Patent No.: US 7,563,786 B2
(45) Date of Patent: Jul. 21, 2009

(54) SUBSTITUTED THIOPHENECARBOXAMIDES, THEIR PREPARATION AND THEIR USE AS MEDICAMENTS

(75) Inventors: Henning Priepke, Warthausen (DE); Kai Gerlach, Biberach (DE); Roland Pfau, Biberach (DE); Wolfgang Wienen, Biberach (DE); Annette Schuler-Metz, Ulm (DE); Herbert Nar, Ochsenhausen (DE); Sandra Handschuh, Warthausen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 152 days.

(21) Appl. No.: 11/238,599

(22) Filed: Sep. 29, 2005

(65) Prior Publication Data
US 2006/0069082 A1 Mar. 30, 2006

(30) Foreign Application Priority Data
Sep. 29, 2004 (DE) .................. 10 2004 047 840

(51) Int. Cl.
A61K 31/535 (2006.01)
C07D 413/12 (2006.01)
(52) U.S. Cl. .................. 514/231.5; 544/146
(58) Field of Classification Search .......... 544/146; 514/231.5
See application file for complete search history.

(56) References Cited
U.S. PATENT DOCUMENTS
2003/0153610 A1 8/2003 Straub et al.

FOREIGN PATENT DOCUMENTS
CA 2506716 6/2004
WO 0147919 7/2001
WO 2004046138 6/2004

OTHER PUBLICATIONS
Qiao et al. Bioorg Med Chem Lett., 17, 2007, 4419-4427.*

* cited by examiner

Primary Examiner—Rebecca L Anderson
(74) Attorney, Agent, or Firm—Michael P. Morris; Edouard G. Lebel; Alan R. Stempel

(57) ABSTRACT

The present invention relates to novel substituted thiophene-2-carboxamides of the general formula

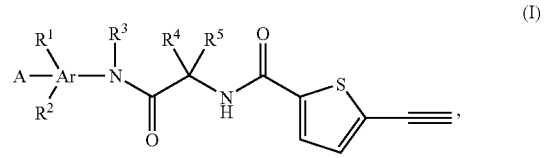

in which A, Ar and $R^1$ to $R^5$ are as defined in claim 1, their tautomers, their enantiomers, their diastereomers, their mixtures and their salts, especially their physiologically acceptable salts with inorganic or organic acids or bases, which have valuable properties.

12 Claims, No Drawings

SUBSTITUTED THIOPHENECARBOXAMIDES, THEIR PREPARATION AND THEIR USE AS MEDICAMENTS

This application claims priority to German Application DE 10 2004 047 840, filed on Sep. 29, 2004, which is incorporated herein in its entirety.

The present invention relates to novel substituted thiophene-2-carboxamides of the general formula

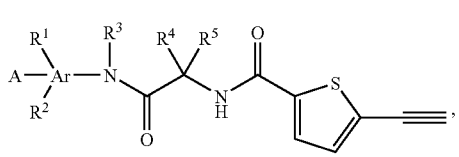

(I)

their tautomers, their enantiomers, their diastereomers, their mixtures and their salts, especially their physiologically acceptable salts with inorganic or organic acids or bases, which have valuable properties.

The compounds of the above general formula I and their tautomers, their enantiomers, their diastereomers, their mixtures and their salts, especially their physiologically acceptable salts with inorganic or organic acids or bases, and their stereoisomers have valuable pharmacological properties, especially an antithrombotic effect and a factor Xa-inhibiting effect.

The present application relates to novel compounds of the above general formula I, their preparation, the medicaments comprising the pharmacologically effective compounds, their preparation and use.

A 1st embodiment of the present invention encompasses those compounds of the general formula I in which A is a group of the general formula

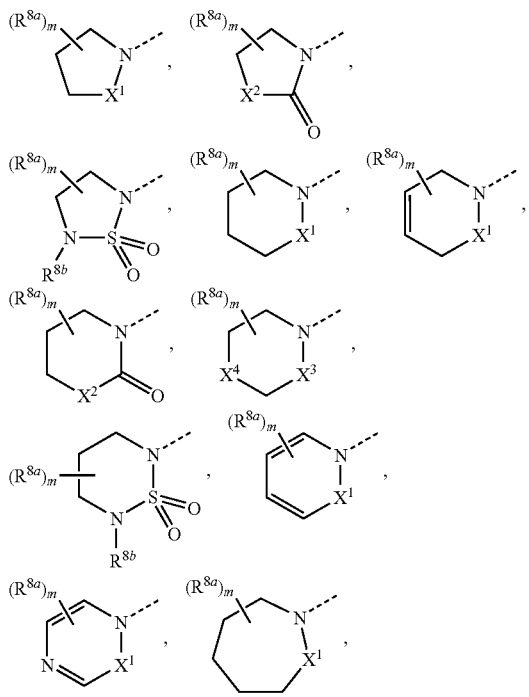

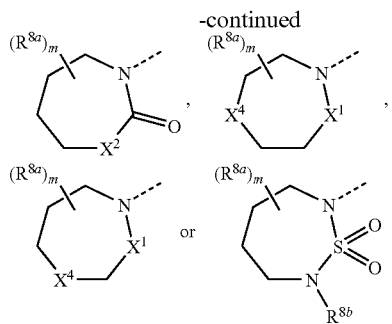

in which m is the number 1 or 2, $R^{8a}$ is in each case independently of one another a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, where in the aforementioned substituted 5- to 7-membered groups A, the heteroatoms F, Cl, Br, I, O or N which may optionally be introduced as substituents with $R^{8a}$, are not separated by exactly one carbon atom from a heteroatom from the group of N, O, S, $R^{8b}$ is in each case independently of one another a hydrogen atom or a $C_{1-5}$-alkyl group, $X^1$ is a carbonyl, thiocarbonyl, $C=NR^{8c}$, $C=N-OR^{8c}$, $C=N-NO_2$, $C=N-CN$ or sulphonyl group, $R^{8c}$ is in each case independently of one another a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^2$ is an oxygen atom or an —$NR^{8b}$-group, where $R^{8b}$ is as defined above, $X^3$ is a carbonyl, thiocarbonyl, $C=NR^{8c}$, $C=N-OR^{8c}$, $C=N-NO_2$, $C=N-CN$ or sulphonyl group, where $R^{8c}$ is as defined above, $X^4$ is an oxygen or sulphur atom or an —$NR^{8c}$-group, where $R^{8c}$ is as defined above, Ar is an aromatic ring selected from the group of phenyl, pyridyl, pyrimidinyl, thienyl, thiazolyl, pyrazolyl, pyrrolyl, $R^1$ is a hydrogen or a halogen atom, a $C_{1-3}$-alkyl or $C_{1-3}$-alkoxy group, where the hydrogen atoms of the $C_{1-3}$-alkyl or $C_{1-3}$-alkoxy group may optionally be wholly or partly replaced by fluorine atoms, or a $C_{2-3}$-alkenyl, $C_{2-3}$-alkynyl, nitrile, nitro or amino group, $R^2$ is a hydrogen or halogen atom or a $C_{1-3}$-alkyl group, $R^3$ is a hydrogen atom or a $C_{1-3}$-alkyl group, $R^4$ and $R^5$ are each independently of one another
a hydrogen atom, a $C_{2-6}$-alkenyl or $C_{2-6}$-alkynyl group,
a straight-chain or branched $C_{1-6}$alkyl group,
where the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, where the hydrogen atoms of the $C_{1-5}$-alkyloxy group may optionally be replaced wholly or partly by fluorine atoms, or an allyloxy, propargyloxy, benzyloxy, $C_{1-5}$-alkylcarbonyloxy, $C_{1-5}$-alkoxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl, di-($C_{1-5}$-alkyl)-aminosulphonyl, $C_{3-6}$-cycloalkyleniminosulphonyl, di-($C_{1-5}$-alkyl)-phosphoryl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkyl-carbonylamino group, a carboxy, aminocarbonyl, $C_{1-5}$-alkylaminocarbonyl, $C_{3-6}$-cycloalkylaminocarbonyl-, di-($C_{1-5}$-alkyl)-aminocarbonyl, $C_{1-5}$-alkoxycarbonyl, $C_{4-6}$-cycloalkyleniminocarbonyl group, a phenyl, heteroaryl, phenyl-$C_{1-5}$-alkyl or heteroaryl-$C_{1-5}$-alkyl group, which may optionally be substituted in the phenyl or heteroaryl moiety once to three times by identical or different substituents selected from the group consisting of halogen atoms, $C_{1-5}$-alkyl, trifluoromethyl, amino, $C_{1-5}$-alkylamino, di-($C_{1-5}$-alkyl)-amino, hydroxy, $C_{1-5}$-alkyloxy, mono-, di- or trifluoromethoxy, carboxy and $C_{1-5}$-alkyloxycarbonyl groups, a 3- to 7-membered cycloalkyl, cycloalkylenimino, cycloalkyl-$C_{1-5}$-alkyl or cycloalkylenimino-$C_{1-3}$-alkyl group, in which in the case of 4- to 7-membered rings a methylene group in the cyclic moiety may optionally be replaced by an —N($R^{8c}$)-group, an oxygen or sulphur atom or an —S(O)— or —S(O)$_2$-group, where $R^{8c}$ is as defined above, or in which in the case of 4- to 7-membered rings two adjacent methylene groups in the cyclic moiety may together optionally be replaced by a —C(O)N($R^{8b}$)— or —S(O)$_2$N($R^{8b}$)-group, where $R^{8b}$ is as defined above, or in which in the case of 6- to 7-membered rings three adjacent methylene groups in the cyclic moiety may together optionally be replaced by a substituted —OC(O)N($R^{8b}$)— or —N($R^{8b}$)C(O)N($R^{8b}$)— or —N($R^{8b}$)S(O)$_2$N($R^{8b}$)-group, where $R^{8b}$ is as defined above, with the proviso that a 3- to 7-membered cycloalkyl, cycloalkylenimino, cycloalkyl-$C_{1-5}$-alkyl or cycloalkylenimino-$C_{1-3}$-alkyl group as defined above, in which two heteroatoms from the group of oxygen and nitrogen are separated from one another by exactly one optionally substituted —CH$_2$— group, is excluded, where a 3- to 7-membered cycloalkyl, cycloalkylenimino, cycloalkyl-$C_{1-5}$-alkyl or cycloalkylenimino-$C_{1-3}$-alkyl group as defined above may be substituted on one or two —CH$_2$—groups by in each case one or two $C_{1-3}$-alkyl groups, or $R^4$ and $R^5$ together with the carbon atom to which they are bonded form a $C_{3-8}$-cycloalkyl or $C_{3-8}$-cycloalkenyl group, where one of the methylene groups of a $C_{4-8}$-cycloalkyl group may be replaced by an oxygen or sulphur atom or an —N($R^{8c}$)— or a carbonyl, sulphinyl or sulphonyl group, where $R^{8c}$ is as defined above, and/or two directly adjacent methylene groups of a $C_{4-8}$-cycloalkyl group may together be replaced by a —C(O)N($R^{8b}$)— or —S(O)$_2$N($R^{8b}$)— group, where $R^{8b}$ is as defined above, and/or three directly adjacent methylene groups of a $C_{6-8}$-cycloalkyl group may together be replaced by a —OC(O)O—, —OC(O)N($R^{8b}$)—, —N($R^{8b}$)C(O)N($R^{8b}$)— or —N($R^{8b}$)S(O)$_2$N($R^{8b}$)— group, where $R^{8b}$ is as defined above, where 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkyl-sulphanyl, $C_{1-5}$alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl-, di-($C_{1-5}$-alkyl)-aminosulphonyl, $C_{3-6}$-cycloalkyleniminosulphonyl, amino-, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino group, where 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl, di-($C_{1-5}$-alkyl)-aminosulphonyl, $C_{3-6}$-cycloalkyleniminosulphonyl group, and 1 to 2 carbon atoms of a $C_{4-8}$-cycloalkenyl group which are not linked by a double bond to another carbon atom may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino group, with the proviso that such a $C_{3-8}$-cycloalkyl or $C_{3-8}$-cycloalkenyl group which is formed together from $R^4$ and $R^5$, in which two heteroatoms in the ring selected from the group of oxygen and nitrogen are separated from one another by exactly one optionally substituted —CH$_2$— group, and/or in which one or both methylene groups in the ring which are directly connected to the carbon atom to which the groups $R^4$ and $R^5$ are attached are replaced by a heteroatom from the group of oxygen, nitrogen and sulphur, and/or in which a substituent which is linked to the cyclic group, and which is distinguished by a heteroatom from the group of oxygen, nitrogen, sulphur and halogen atom being directly linked to the cyclic group, is separated from another heteroatom from the group of oxygen, nitrogen and sulphur, with the exception of the sulphone group, by exactly one optionally substituted methylene group, and/or in which two oxygen atoms are directly connected together, is excluded, where, unless otherwise mentioned, the term "heteroaryl group" mentioned above in the definitions means a monocyclic 5- or 6-membered heteroaryl group, where the 6-membered heteroaryl group comprises one, two or three nitrogen atoms and the 5-membered heteroaryl group comprises an imino group which is optionally substituted by a $C_{1-3}$-alkyl, phenyl or phenyl-$C_{1-3}$-alkyl group, or an oxygen or sulphur atom or an imino group which is optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkylenimino-$C_{1-3}$-alkyl or phenyl-$C_{1-3}$-alkyl group, or an oxygen or sulphur atom and additionally a nitrogen atom or an imino group which is optionally substituted by a $C_{1-3}$-alkyl or phenyl-$C_{1-3}$-alkyl group, and two or three nitrogen atoms, and additionally a phenyl ring which is optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkylenimino group may be fused to the aforementioned monocyclic heteroaryl groups via two adjacent carbon atoms, and the linkage takes place via a nitrogen atom or via a carbon atom of the heterocyclic moiety or of a fused phenyl ring, where, unless otherwise mentioned, the term "halogen atom" mentioned above in the definitions means an atom from the group of fluorine, chlorine, bromine and iodine, where the alkyl, alkenyl, alkynyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different, and where the hydrogen atoms in the methyl or ethyl groups present in the aforementioned definitions may, unless otherwise mentioned, be wholly or partly replaced by fluorine atoms, their tautomers, their enantiomers, their diastereomers, their mixtures and their salts.

Examples of monocyclic heteroaryl groups are the pyridyl, N-oxypyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]isothiazolyl, benzo[d]isothiazolyl, benzooxazolyl, benzo[c]isoxazolyl, benzo[d]isoxazolyl, benzo[1,2,5]oxadiazolyl-benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxyquinolinyl, isoquinolinyl, quinazolinyl, N-oxyquinazolinyl, quinoxalinyl, phthalazinyl, indolyl, isoindolyl or 1-oxa-2,3-diazaindenyl group.

Examples of the $C_{1-6}$-alkyl groups mentioned above in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned above in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-6}$-alkenyl groups mentioned above in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl, 2-ethylprop-2-en-1-yl, hex-1-en-2-yl, hex-2-en-2-yl, hex-3-en-2-yl, hex-4-en-2-yl, hex-5-en-2-yl, hex-1-en-3-yl, hex-2-en-3-yl, hex-3-en-3-yl, hex-4-en-3-yl, hex-5-en-3-yl, hex-1-en-4-yl, hex-2-en-4-yl, hex-3-en-4-yl, hex-4-en-4-yl, hex-5-en-4-yl, 4-methyl-pent-1-en-3-yl, 3-methyl-pent-1-en-3-yl, 2-methyl-pent-1-en-3-yl, 2,3-dimethyl-but-1-en-3-yl, 3,3-dimethyl-but-1-en-2-yl or 2-ethyl-but-1-en-3-yl group.

Examples of the $C_{2-6}$-alkynyl groups mentioned above in the definitions are the ethyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl, 3-methyl-1-butyn-3-yl, 1-hexyn-1-yl, 2-hexyn-1-yl, 3-hexyn-1-yl, 4-hexyn-1-yl, 5-hexyn-1-yl, 1-hexyn-3-yl, 1-hexyn-4-yl, 1-hexyn-5-yl, 2-hexyn-4-yl, 2-hexyn-5-yl, 3-hexyn-5-yl, 3-methyl-1-perityn-3-yl, 4-methyl-1-pentyn-3-yl, 3-methyl-1-pentyn-4-yl, 4-methyl-1-pentyn-4-yl, 4-methyl-2-pentyn-4-yl, 4-methyl-2-pentyn-1-yl, 2,2-dimethyl-3-butyn-1-yl or 2-ethyl-3-butyn-1-yl group.

A 2nd embodiment of the present invention encompasses those compounds of the general formula I in which A is a group of the general formula

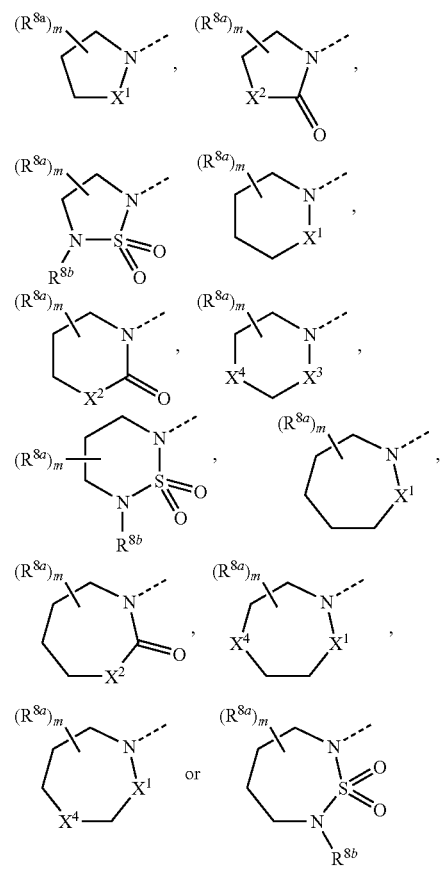

in which m is the number 1 or 2, $R^{8a}$ is in each case independently of one another a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, where in the aforementioned substituted 5- to 7-membered groups A, the heteroatoms F, Cl, Br, I, O or N which may optionally be introduced as substituents with $R^{8a}$, are not separated by exactly one carbon atom from a heteroatom from the group of N, O, S, $R^{8b}$ is in each case independently of one another a hydrogen atom or a $C_{1-3}$-alkyl group, $X^1$ is a carbonyl, thiocarbonyl, C=$NR^{8c}$, C=N—$OR^{8c}$, C=N—$NO_2$, C=N—CN or sulphonyl group, $R^{8c}$ is in each case independently of one another a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^2$ is an oxygen atom or a —$NR^{8b}$-group, where $R^{8b}$ is as defined above, $X^3$ is a carbonyl, thiocarbonyl, C=$NR^{8c}$, C=N—$OR^c$, C=N—$NO_2$, C=N—CN or sulphonyl group, where $R^{8c}$ is as defined above, $X^4$ is an oxygen atom or a —$NR^{8c}$-group, where $R^{8c}$ is as defined above, Ar is an aromatic ring selected from the group of phenyl, pyridyl, pyrimidinyl, thienyl, thiazolyl, pyrazolyl, pyrrolyl, $R^1$ is a hydrogen or a halogen atom, a $C_{1-3}$-alkyl or $C_{1-3}$-alkoxy group, where the hydrogen atoms of the $C_{1-3}$-alkyl or $C_{1-3}$-alkoxy group may optionally be replaced wholly or partly by fluorine atoms, or a nitrile group, $R^2$ is a hydrogen or halogen atom or a methyl group, $R^3$ is a hydrogen atom or a methyl group, $R^4$ is a $C_{2-6}$-alkenyl or $C_{2-6}$-alkynyl group, a straight-chain or branched $C_{1-6}$-alkyl group, where the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, where the hydrogen atoms of the $C_{1-5}$-alkyloxy group may optionally be replaced wholly or partly by fluorine atoms, or a benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl, di-($C_{1-5}$-alkyl)-aminosulphonyl, $C_{3-6}$-cycloalkyleniminosulphonyl, di-($C_{1-5}$-alkyl)-phosphoryl, amino, $C_{1-5}$-alkylamino, di-($C_{1-5}$-alkyl)-amino, $C_{1-5}$-alkylcarbonylamino, $C_{1-5}$-alkylsulphonylamino, or an N—($C_{1-5}$-alkylsulphonyl)-$C_{1-5}$-alkylamino group, a carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkoxycarbonyl, $C_{4-6}$-cycloalkyleniminocarbonyl group, a phenyl, heteroaryl, phenyl-$C_{1-5}$-alkyl or heteroaryl-$C_{1-5}$-alkyl group, which may optionally be substituted in the phenyl or heteroaryl moiety once to three times by identical or different substituents selected from the group consisting of halogen atoms, $C_{1-5}$-alkyl, trifluoromethyl, amino, $C_{1-5}$-alkyl-amino-, di-($C_{1-5}$-alkyl)-amino, hydroxy, $C_{1-5}$-alkyloxy, mono-, di- or trifluoromethoxy, carboxy and $C_{1-5}$-alkyloxycarbonyl groups, a 3- to 7-membered cycloalkyl, cycloalkylenimino, cycloalkyl-$C_{1-5}$-alkyl or cycloalkylenimino-$C_{1-3}$-alkyl group, in which in the case of 4- to 7-membered rings a methylene group in the cyclic moiety may optionally be replaced by an —N($R^{8c}$)— group, an oxygen or sulphur atom or an —S(O)— or —S(O)$_2$— group, where $R^{8c}$ is as defined above, or in which in the case of 4- to 7-membered rings two adjacent methylene groups in the cyclic moiety may together optionally be replaced by a —C(O)N($R^{8b}$)— or —S(O)$_2$N($R^{8b}$)— group, where $R^{8b}$ is as defined above, or in which in the case of 6- to 7-membered rings three adjacent methylene groups in the cyclic moiety may together optionally be replaced by a substituted —OC(O)N($R^{8b}$)— or —N($R^{8b}$)C(O)N($R^{8b}$)— or —N($R^{8b}$)S(O)$_2$N($R^{8b}$)— group, where $R^{8b}$ is as defined above, with the proviso that a 3- to 7-membered cycloalkyl, cycloalkylenimino, cycloalkyl-$C_{1-5}$-alkyl or cycloalkylenimino-$C_{1-3}$-alkyl group which is as defined above and in which two heteroatoms selected from the group of oxygen and nitrogen are separated from one another by exactly one optionally substituted —$CH_2$— group is excluded, where a 3- to 7-membered cycloalkyl, cycloalkylenimino, cycloalkyl-$C_{1-5}$-alkyl or cycloalkylenimino-$C_{1-3}$-alkyl group as defined above may be substituted on one or two —$CH_2$— groups by in each case one or two $C_{1-3}$-alkyl groups, $R^5$ is a hydrogen atom, a $C_{2-6}$-alkenyl or $C_{2-6}$-alkynyl group, a straight-chain or branched $C_{1-6}$-alkyl group, where the hydrogen atoms of the straight-chain or branched $C_{1-6}$-alkyl group may optionally be replaced wholly or partly by fluorine atoms, and which may optionally be substituted by a $C_{1-5}$-alkyloxy group, where the hydrogen atoms of the $C_{1-5}$-alkyloxy group may optionally be replaced wholly or partly by fluorine atoms, or $R^4$ and $R^5$ together with the carbon atom to which they are bonded form a $C_{3-8}$-cycloalkyl or $C_{3-8}$-cycloalkenyl group, where one of the methylene groups of a $C_{4-8}$-cycloalkyl group may be replaced by an oxygen or sulphur atom or an —N($R^{8c}$)— group or a carbonyl or sulphonyl group, where $R^{8c}$ is as defined above, and/or two directly adjacent methylene groups of a $C_{4-8}$-cycloalkyl group may together be replaced by a —C(O)N($R^{8b}$)— or —S(O)$_2$N($R^{8b}$)— group, where $R^{8b}$ is as defined above, and/or three directly adjacent methylene groups of a $C_{6-8}$-cycloalkyl group may together be replaced by a —OC(O)O—, —OC(O)N($R^{8b}$)—, —N($R^{8b}$)C(O)N($R^{8b}$)— or —N($R^{8b}$)S(O)$_2$N($R^{8b}$)— group, where $R^{8b}$ is as defined above, where 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl, di-($C_{1-5}$-alkyl)-aminosulphonyl, $C_{3-6}$cycloalkyleniminosulphonyl, amino, $C_{1-5}$-alkylamino, di-($C_{1-5}$-alkyl)-amino, $C_{1-5}$-alkylcarbonylamino, $C_{1-5}$-alkylsulphonylamino or N—($C_{1-5}$-alkylsulphonyl)-$C_{1-5}$-alkyl-amino groups, where 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl, di-($C_{1-5}$-alkyl)-aminosulphonyl, $C_{3-6}$-cycloalkyleniminosulphonyl group, and 1 to 2 carbon atoms of a $C_{4-8}$-cycloalkenyl group which are not linked by a double bond to another carbon atom may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino group, with the proviso that such a $C_{3-8}$-cycloalkyl or $C_{3-8}$-cycloalkenyl group formed together from $R^4$ and $R^5$ in which two heteroatoms in the ring selected from the group of oxygen and nitrogen are separated from one another by exactly one optionally substituted —$CH_2$— group, and/or in which one or both methylene groups in the ring which are connected directly to the carbon atom to which the groups $R^4$ and $R^5$ are attached are replaced by a heteroatom from the group of oxygen, nitrogen and sulphur, and/or in which a substituent which is linked to the cyclic group, and which is distinguished by a heteroatom from the group of oxygen, nitrogen, sulphur and halogen atom being directly linked to the cyclic group, is separated from another heteroatom from the group of oxygen, nitrogen and sulphur, with the exception of the sulphone group, by exactly one optionally substituted methylene group, and/or in which two oxygen atoms are directly connected together, is excluded, where, unless otherwise mentioned, the term "heteroaryl group" mentioned above in the definitions means a monocyclic 5- or 6-membered heteroaryl group, where the 6-membered heteroaryl group comprises one, two or three nitrogen atoms and the 5-membered heteroaryl group comprises an imino group which is optionally substituted by a $C_{1-3}$-alkyl, phenyl or phenyl-$C_{1-3}$-alkyl group, or an oxygen or sulphur atom or an imino group which is optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkylenimino-$C_{1-3}$-alkyl or phenyl-$C_{1-3}$-alkyl group, or an oxygen or sulphur atom and additionally a nitrogen atom or an imino group which is optionally substituted by a $C_{1-3}$-alkyl or phenyl-$C_{1-3}$-alkyl group, and two or three nitrogen atoms, and additionally a phenyl ring which is optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkylenimino group may be fused to the aforementioned monocyclic heteroaryl groups via two adjacent carbon atoms, and the linkage takes place via a nitrogen atom or via a carbon atom of the heterocyclic moiety or of a fused phenyl ring, where, unless otherwise mentioned, the term "halogen atom" mentioned above in the definitions means an atom from the group of fluorine, chlorine, bromine and iodine, where the alkyl, alkenyl, alkynyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different, and where the hydrogen atoms in the methyl or ethyl groups present in the aforementioned definitions may, unless otherwise mentioned, be wholly or partly replaced by fluorine atoms, their tautomers, their enantiomers, their diastereomers, their mixtures and their salts.

A 3rd embodiment of the present invention encompasses those compounds of the general formula I in which A is a group of the general formula

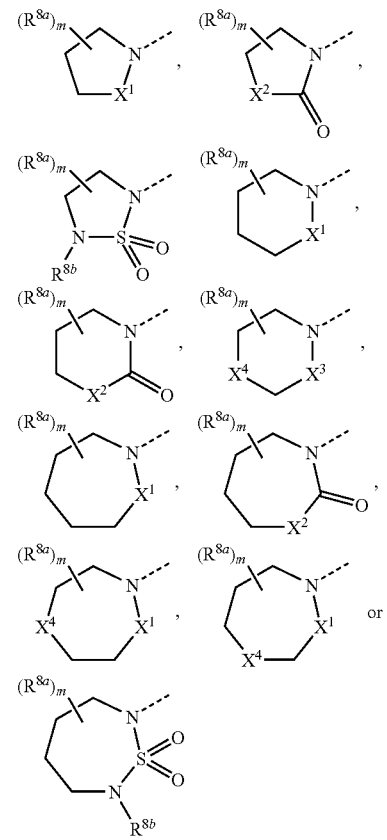

in which m is the number 1 or 2, $R^{8a}$ is in each case independently of one another a hydrogen or a fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylaminocarbonyl, di-($C_{1-3}$-alkyl)-aminocarbonyl or $C_{1-3}$-alkylcarbonylamino group, where in the aforementioned substituted 5- to 7-membered groups A, the heteroatoms F, O or N which may optionally be introduced as substituents with $R^{8a}$, are not separated by exactly one carbon atom from a heteroatom from the group of N, O, S, $R^{8b}$ is in each case independently of one another a hydrogen atom or a $C_{1-3}$-alkyl group, $X^1$ is a carbonyl, thiocarbonyl, C=$NR^{8c}$, C=N—$OR^{8c}$, C=N—CN or sulphonyl group, $R^{8c}$ is in each case independently of one another a hydrogen atom, a $C_{1-3}$-alkyl, $C_{1-3}$-alkylcarbonyl, $C_{1-4}$-alkyloxycarbonyl or $C_{1-3}$-alkylsulphonyl group, $X^2$ is an oxygen atom or an —$NR^{8b}$-group, where $R^{8b}$ is as defined above, $X^3$ is a carbonyl, thiocarbonyl, C=$NR^{8c}$, C=N—$OR^{8c}$, C=N—CN or sulphonyl group, where $R^{8c}$ is as defined above, $X^4$ is an oxygen atom or an —$NR^{8c}$-group, where $R^{8c}$ is as defined above, Ar is an aromatic ring selected from the group of phenyl, pyridyl, pyrimidinyl, thienyl, thiazolyl, pyrazolyl, pyrrolyl, $R^1$ is a hydrogen, fluorine, chlorine, bromine or iodine atom, a $C_{1-3}$-alkyl or $C_{1-3}$-alkoxy group, where the hydrogen atoms of the $C_{1-3}$-alkyl or $C_{1-3}$-alkoxy group may optionally be replaced wholly or partly by fluorine atoms, $R^2$ is a hydrogen or halogen atom or a methyl group, $R^3$ is a hydrogen atom, $R^4$ is a $C_{2-4}$-alkenyl or $C_{2-4}$-alkynyl group, a straight-chain or branched $C_{1-6}$-alkyl group,
where the hydrogen atoms of the straight-chain or branched $C_{1-6}$-alkyl group may optionally be replaced wholly or partly by fluorine atoms, and which may optionally be substituted by a $C_{3-5}$-cycloalkyl group, a nitrile, hydroxy, a $C_{1-5}$-alkyloxy group, where the hydrogen atoms of the $C_{1-5}$-alkyloxy group may optionally be replaced wholly or partly by fluorine atoms, or $C_{1-5}$-alkylcarbonyloxy, $C_{1-5}$-alkoxycarbonyloxy, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl, di-($C_{1-5}$-alkyl)-aminosulphonyl, $C_{3-6}$-cycloalkyleniminosulphonyl, di-($C_{1-5}$-alkyl)-phosphoryl, amino, $C_{1-5}$-alkylamino, di-($C_{1-5}$-alkyl)-amino, $C_{1-5}$-alkylcarbonylamino, $C_{1-5}$-alkylsulphonylamino, or an N—($C_{1-5}$-alkylsulphonyl)-$C_{1-5}$-alkylamino group, a phenyl, heteroaryl, phenyl-$C_{1-3}$-alkyl or heteroaryl-$C_{1-3}$-alkyl group, which may optionally be substituted in the phenyl or heteroaryl moiety once to three times by identical or different substituents selected from the group consisting of halogen atoms, $C_{1-3}$-alkyl, trifluoromethyl, amino, $C_{1-3}$-alkylamino, di-($C_{1-3}$-alkyl)-amino, hydroxy, $C_{1-3}$-alkyloxy, mono-, di- or trifluoromethoxy, carboxy and $C_{1-3}$-alkyloxycarbonyl groups, $R^5$ is a hydrogen atom, a $C_{2-4}$-alkenyl or $C_{2-4}$-alkynyl group or a straight-chain or branched $C_{1-4}$-alkyl group,
where the hydrogen atoms of the straight-chain or branched $C_{1-4}$-alkyl group may optionally be replaced wholly or partly by fluorine atoms, and which may optionally be substituted by a $C_{1-3}$-alkyloxy group, where the hydrogen atoms of the $C_{1-3}$-alkyloxy group may optionally be wholly or partly replaced by fluorine atoms, or $R^4$ and $R^5$ together with the carbon atom to which they are bonded form a $C_{3-8}$-cycloalkyl or $C_{3-8}$-cycloalkenyl group, where one of the methylene groups of a $C_{4-8}$-cycloalkyl group may be replaced by an oxygen or sulphur atom or a carbonyl, sulphonyl or —N($R^{8c}$)— group, where $R^{8c}$ is as defined above, and/or two directly adjacent methylene groups of a $C_{4-8}$-cycloalkyl group may together be replaced by a —C(O)N($R^{8b}$)— or —S(O)$_2$N($R^{8b}$)— group, where $R^{8b}$ is as defined above, and/or three directly adjacent methylene groups of a $C_{6-8}$-cycloalkyl group may together be replaced by a —OC(O)O, —OC(O)N($R^{8b}$)—, —N($R^{8b}$)C(O)N($R^{8b}$)— or —N($R^{8b}$)S(O)$_2$N($R^{8b}$)— group, where $R^{8b}$ is as defined above, where 1 to 3 carbon atoms of a $C_{3-8}$-cycloalkyl group may optionally be substituted independently of one another by a $C_{1-3}$-alkyl, hydroxy, $C_{1-3}$-alkyloxy, $C_{1-3}$-alkylcarbonyloxy, $C_{1-3}$-alkyloxycarbonyl, amino, $C_{1-3}$-alkylamino, di-($C_{1-3}$-alkyl)-amino, $C_{1-3}$-alkylcarbonylamino, $C_{1-3}$-alkylsulphonylamino group, where 1 to 2 carbon atoms of a $C_{3-8}$-cycloalkenyl group may optionally be substituted independently of one another by a $C_{1-3}$-alkyl group, and 1 to 2 carbon atoms of a $C_{4-8}$-cycloalkenyl group which are not linked by a double bond to another carbon atom may optionally be substituted independently of one another by a hydroxy, $C_{1-3}$-alkyloxy, di-($C_{1-3}$-alkyl)-amino group, with the proviso that such a $C_{3-8}$-cycloalkyl or $C_{3-8}$-cycloalkenyl group formed together from $R^4$ and $R^5$ in which two heteroatoms in the ring selected from the group of oxygen and nitrogen are separated from one another by exactly one optionally substituted —CH$_2$— group, and/or in which one or both methylene groups in the ring which are connected directly to the carbon atom to which the groups $R^4$ and $R^5$ are attached are replaced by a heteroatom from the group of oxygen, nitrogen and sulphur, and/or in which a substituent which is linked to the cyclic group, and which is distinguished by a heteroatom from the group of oxygen, nitrogen, sulphur and halogen atom being directly linked to the cyclic group, is separated from another heteroatom from the group of oxygen, nitrogen and sulphur, with the exception of the sulphone group, by exactly one optionally substituted methylene group, and/or in which two oxygen atoms are directly connected together, is excluded, where, unless otherwise mentioned, the term "heteroaryl group" mentioned above in the definitions means a monocyclic 5- or 6-membered heteroaryl group, where the 6-membered heteroaryl group comprises one, two or three nitrogen atoms and the 5-membered heteroaryl group comprises an imino group which is optionally substituted by a $C_{1-3}$-alkyl, phenyl or phenyl-$C_{1-3}$-alkyl group, or an oxygen or sulphur atom or an imino group which is optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkylenimino-$C_{1-3}$-alkyl or phenyl-$C_{1-3}$-alkyl group, or an oxygen or sulphur atom and additionally a nitrogen atom or an imino group which is optionally substituted by a $C_{1-3}$-alkyl or phenyl-$C_{1-3}$-alkyl group, and two or three nitrogen atoms, and additionally a phenyl ring which is optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkylenimino group may be fused to the aforementioned monocyclic heteroaryl groups via two adjacent carbon atoms, and the linkage takes place via a nitrogen atom or via a carbon atom of the heterocyclic moiety or of a fused phenyl ring, where, unless otherwise mentioned, the term "halogen atom" mentioned above in the definitions means an atom from the group of fluorine, chlorine, bromine and iodine, where the alkyl, alkenyl, alkynyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different, and where the hydrogen atoms in the methyl or ethyl groups present in the aforementioned definitions may, unless otherwise mentioned, be wholly or partly replaced by fluorine atoms, their tautomers, their enantiomers, their diastereomers, their mixtures and their salts.

A 4th embodiment of the present invention encompasses those compounds of the general formula I in which A is a group of the general formula

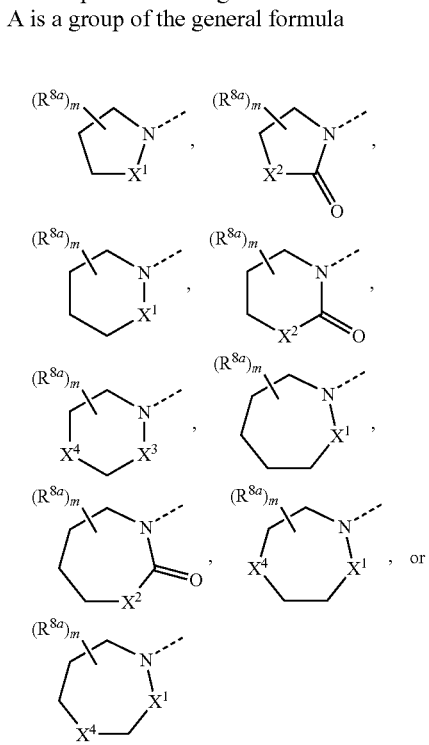

in which m is the number 1 or 2, $R^{8a}$ is in each case independently of one another a hydrogen atom or a $C_{1-3}$-alkyl, hydroxy, hydroxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, where in the aforementioned substituted 5- to 7-membered groups A, the heteroatoms O or N which may optionally be introduced as substituents with $R^{8a}$, are not separated by exactly one carbon atom from a heteroatom from the group of N, O, S, $R^{8b}$ is in each case independently of one another a hydrogen atom or a $C_{1-3}$-alkyl group, $X^1$ is a carbonyl, $C=NR^{8c}$, $C=N-OR^{8c}$, $C=N-CN$ or sulphonyl group, $R^{8c}$ is in each case independently of one another a hydrogen atom, a $C_{1-3}$-alkyl, $C_{1-3}$-alkylcarbonyl, or a $C_{1-4}$-alkyloxycarbonyl group, $X^2$ is an oxygen atom or an —$NR^{8b}$-group, where $R^{8b}$ is as defined above, $X^3$ is a carbonyl, $C=NR^{8c}$, $C=N-OR^{8c}$, $C=N-CN$ or sulphonyl group, where $R^{8c}$ is as defined above, $X^4$ is an oxygen atom or an —$NR^{8c}$-group, where $R^{8c}$ is as defined above, Ar is a phenyl or pyridyl group, $R^1$ is a hydrogen, fluorine, chlorine, bromine or iodine atom, a methyl or a methoxy group, where the hydrogen atoms of the methyl or methoxy group may optionally be wholly or partly replaced by fluorine atoms, $R^2$ is a hydrogen or fluorine atom or a methyl group, $R^3$ is a hydrogen atom, $R^4$ is a $C_{2-4}$-alkenyl or $C_{2-4}$-alkynyl group, a straight-chain or branched $C_{1-6}$alkyl group, where the hydrogen atoms of the straight-chain or branched $C_{1-6}$alkyl group may optionally be replaced wholly or partly by fluorine atoms, and which may optionally be substituted by a $C_{3-5}$-cycloalkyl group, a nitrile, hydroxy, a $C_{1-5}$-alkyloxy group, where the hydrogen atoms of the $C_{1-5}$-alkyloxy group may optionally be replaced wholly or partly by fluorine atoms, or $C_{1-5}$-alkylcarbonyloxy, $C_{1-5}$-alkyloxycarbonyloxy, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl, di-($C_{1-5}$-alkyl)-aminosulphonyl, $C_{3-6}$-cycloalkyleniminosulphonyl, di-($C_{1-5}$-alkyl)-phosphoryl, amino, $C_{1-5}$-alkylamino, di-($C_{1-5}$-alkyl)-amino, $C_{1-5}$-alkylcarbonylamino, $C_{1-5}$-alkylsulphonylamino, or an N—($C_{1-5}$-alkylsulphonyl)-$C_{1-5}$-alkylamino group, a phenyl, heteroaryl, phenyl-$C_{1-3}$-alkyl or heteroaryl-$C_{1-3}$-alkyl group, which may optionally be substituted in the phenyl or heteroaryl moiety once to three times by identical or different substituents selected from the group consisting of halogen atoms, $C_{1-3}$-alkyl, di-($C_{1-3}$-alkyl)-amino, hydroxy, $C_{1-3}$-alkyloxy, mono-, di- and trifluoromethoxy groups, $R^5$ is a hydrogen atom or a straight-chain or branched $C_{1-4}$-alkyl group, where the hydrogen atoms of the straight-chain or branched $C_{1-4}$-alkyl group may optionally be wholly or partly replaced by fluorine atoms, or $R^4$ and $R^5$ together with the carbon atom to which they are bonded form a $C_{3-8}$-cycloalkyl group, where one of the methylene groups of a $C_{4-8}$-cycloalkyl group may be replaced by an oxygen or sulphur atom or a sulphonyl or —N($R^{8c}$)-group, where $R^{8c}$ is as defined above, and/or two directly adjacent methylene groups of a $C_{4-8}$-cycloalkyl group may together be replaced by a —C(O)N($R^{8b}$)— or —S(O)$_2$N($R^{8b}$)— group, where $R^{8b}$ is as defined above, and/or three directly adjacent methylene groups of a $C_{6-8}$-cycloalkyl group may together be replaced by a —OC(O)O—, —OC(O)N($R^{8b}$)—, —N($R^{8b}$)C(O)N($R^{8b}$)— or —N($R^{8b}$)S(O)$_2$N($R^{8b}$)— group, where $R^{8b}$ is as defined above, where 1 to 2 carbon atoms of a $C_{3-8}$-cycloalkyl group may optionally be substituted independently of one another by a $C_{1-3}$-alkyl, hydroxy, $C_{1-3}$-alkyloxy, $C_{1-3}$-alkyloxycarbonyl, $C_{1-3}$-alkylamino, di-($C_{1-3}$-alkyl)-amino group, with the proviso that such a $C_{3-8}$-cycloalkyl group formed together from $R^4$ and $R^5$ in which two heteroatoms in the ring selected from the group of oxygen and nitrogen are separated from one another by exactly one optionally substituted —CH$_2$— group, and/or in which one or both methylene groups in the ring which are connected directly to the carbon atom to which the groups $R^4$ and $R^5$ are attached are replaced by a heteroatom from the group of oxygen, nitrogen and sulphur, and/or in which a substituent which is linked to the cyclic group, and which is distinguished by a heteroatom from the group of oxygen, nitrogen, sulphur and halogen atom being directly linked to the cyclic group, is separated from another heteroatom from the group of oxygen, nitrogen and sulphur, with the exception of the sulphone group, by exactly one optionally substituted methylene group, and/or in which two oxygen atoms are directly connected together, is excluded, where, unless otherwise mentioned, the term "heteroaryl group" mentioned above in the definitions means a monocyclic 5- or 6-membered heteroaryl group, where the 6-membered heteroaryl group comprises one, two or three nitrogen atoms, and the 5-membered heteroaryl group comprises an imino group which is optionally substituted by a $C_{1-3}$-alkyl, phenyl or phenyl-$C_{1-3}$-alkyl group, or an oxygen or sulphur atom or an imino group which is optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkylenimino-$C_{1-3}$-alkyl or phenyl-$C_{1-3}$-alkyl group, or an oxygen or sulphur atom and additionally a nitrogen atom or an imino group which is optionally substituted by a $C_{1-3}$-alkyl or phenyl-$C_{1-3}$-alkyl group, and two or three nitrogen atoms, and additionally a phenyl ring which is optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkylenimino group may be fused to the aforementioned monocyclic heteroaryl groups via two adjacent carbon atoms, and the linkage takes place via a nitrogen atom or via a carbon atom of the heterocyclic moiety or of a fused phenyl ring, where, unless otherwise mentioned, the term "halogen atom" mentioned above in the definitions means an atom from the group of fluorine, chlorine, bromine and iodine, where the alkyl, alkynyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different, and where the hydrogen atoms in the methyl or ethyl groups present in the aforementioned definitions may, unless otherwise mentioned, be wholly or partly replaced by fluorine atoms, their tautomers, their enantiomers, their diastereomers, their mixtures and their salts.

A 5th embodiment of the present invention encompasses those compounds of the general formula I in which A is a group of the general formula in which m is the number 1 or 2, $R^{8a}$ is in each case independently of one another a hydrogen atom or a $C_{1-3}$-alkyl group, $X^1$ is a carbonyl, C=NH, C=N—OH, C=N—CN or sulphonyl group, $X^2$ is an oxygen atom or an —NR$^{8b}$-group, $R^{8b}$ is a hydrogen atom or a $C_{1-3}$-alkyl group, $X^3$ is a carbonyl, C=NH, C=N—OH, C=N—CN or sulphonyl group, $X^4$ is an oxygen atom or an —NR$^{8c}$-group, $R^{8c}$ is a hydrogen atom, a $C_{1-3}$-alkyl, $C_{1-3}$-alkylcarbonyl, or a $C_{1-4}$-alkyloxycarbonyl group, Ar is a phenyl or pyridyl group, $R^1$ is a hydrogen, fluorine, chlorine, bromine or iodine atom, a methyl or a trifluoromethyl group, $R^2$ is a hydrogen or fluorine atom, $R^3$ is a hydrogen atom, $R^4$ is a straight-chain or branched $C_{1-6}$-alkyl group, where the hydrogen atoms of the straight-chain or branched $C_{1-6}$-alkyl group may optionally be wholly or partly replaced by fluorine atoms, and which may optionally be substituted by a hydroxy, a $C_{1-5}$-alkyloxy group, $C_{1-5}$-alkylsulphanyl, $C_{1-5}$-alkylsulphinyl, $C_{1-5}$-alkylsulphonyl, carboxy, $C_{1-5}$-alkyloxycarbonyl, di-($C_{1-5}$-alkyl)-phosphoryl group, a phenyl, phenyl-$C_{1-2}$-alkyl, heteroaryl-$C_{1-2}$-alkyl or C-linked heteroaryl group, where the heteroaryl group is selected from the group consisting of imidazolyl, furanyl, pyrazolyl, tetrazolyl and pyridinyl, and which may optionally be substituted in the phenyl or heteroaryl moiety once to twice by identical or different substituents selected from chlorine or fluorine atoms or $C_{1-3}$-alkyl groups, $R^5$ is a hydrogen atom or a straight-chain or branched $C_{1-4}$-alkyl group, where the hydrogen atoms of the straight-chain or branched $C_{1-4}$-alkyl group may optionally be replaced wholly or partly by fluorine atoms, or $R^4$ and $R^5$ together with the carbon atom to which they are bonded form a $C_{3-7}$-cycloalkyl group, where one of the methylene groups of a $C_{4-8}$-cycloalkyl group may be replaced by an oxygen or sulphur atom or a sulphonyl or —N($R^{8c}$)— group, where $R^{8c}$ is as defined above, and/or two directly adjacent methylene groups of a $C_{4-8}$-cycloalkyl group may together be replaced by a —C(O)N($R^{8b}$)— or —S(O)$_2$N($R^{8b}$)-group, where $R^{8b}$ is as defined above, and/or three directly adjacent methylene groups of a $C_{6-8}$-cycloalkyl group may together be replaced by a —OC(O)O—, —OC(O)N($R^{8b}$)—, —N($R^{8b}$)C(O)N($R^{8b}$)— or —N($R^{8b}$)S(O)$_2$N($R^{8b}$)— group, where $R^{8b}$ is as defined above, where 1 to 2 carbon atoms of a $C_{3-7}$-cycloalkyl group may optionally be substituted independently of one another by a $C_{1-3}$-alkyl, hydroxy, $C_{1-3}$-alkyloxy or di-($C_{1-3}$-alkyl)-amino group, with the proviso that such a $C_{3-7}$-cycloalkyl group formed together from $R^4$ and $R^5$, in which two heteroatoms in the ring selected from the group of oxygen and nitrogen are separated from one another by exactly one optionally substituted —CH$_2$— group, and/or in which one or both methylene groups of the ring which are directly connected to the carbon atom to which the groups $R^4$ and $R^5$ are attached are replaced by a heteroatom from the group of oxygen, nitrogen and sulphur, and/or in which a substituent which is linked to the cyclic group, and which is distinguished in that an oxygen or nitrogen atom is directly linked to the cyclic group, is separated from another heteroatom from the group of oxygen, nitrogen and sulphur, with the exception of the sulphone group, by exactly one, optionally substituted methylene group, and/or in which two oxygen atoms are directly connected together, is excluded, where, unless mentioned otherwise, the term "halogen atom" mentioned above in the definitions means an atom from the group of fluorine, chlorine, bromine and iodine, where the alkyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different, and where the hydrogen atoms in the methyl or ethyl groups present in the aforementioned definitions may, unless otherwise mentioned, be wholly or partly replaced by fluorine atoms, their tautomers, their enantiomers, their diastereomers, their mixtures and their salts.

A 6th embodiment of the present invention encompasses those compounds of the general formula I in which A is a group of the general formula in which m is the number 1 or 2, $R^{8a}$ is in each case independently of one another a hydrogen atom or a $C_{1-3}$-alkyl group, $X^1$ is a carbonyl, C=NH, C=N—OH, C=N—CN or sulphonyl group, $X^2$ is an oxygen atom or an —NR$^{8b}$-group, $R^{8b}$ is a hydrogen atom or a $C_{1-3}$-alkyl group, $X^3$ is a carbonyl, C=NH, C=N—OH, C'N—CN or sulphonyl group, $X^4$ is an oxygen atom or an —NR$^{8c}$-group, $R^{8c}$ is a hydrogen atom, a $C_{1-3}$-alkyl, $C_{1-3}$-alkylcarbonyl, or a $C_{1-4}$-alkyloxycarbonyl group, Ar is a phenyl or pyridyl group, $R^1$ is a hydrogen, chlorine or bromine atom, a methyl or trifluoromethyl group, $R^2$ is a hydrogen or fluorine atom, $R^3$ is a hydrogen atom, $R^4$ is a trifluoromethyl group, a straight-chain or branched $C_{1-4}$-alkyl group which may optionally be substituted by a hydroxy, a $C_{1-5}$-alkyloxy group, $C_{1-5}$-alkylsulphanyl, $C_{1-5}$-alkylsulphinyl, $C_{1-5}$-alkylsulphonyl, carboxy, $C_{1-5}$-alkyloxycarbonyl, di-($C_{1-5}$-alkyl)-phosphoryl group, a phenyl, benzyl, heteroaryl-$C_{1-2}$-alkyl or C-linked heteroaryl group, where the heteroaryl group is selected from the group consisting of imidazolyl, furanyl, pyrazolyl, tetrazolyl and pyridinyl, and which may optionally be substituted in the phenyl or heteroaryl moiety once to twice by identical or different substituents selected from chlorine or fluorine atoms or $C_{1-3}$-alkyl groups, $R^5$ is a hydrogen atom or a methyl group, or R⁴ and R⁵ together with the carbon atom to which they are bonded form a $C_{3-6}$-cycloalkyl group,
  where one of the methylene groups of a $C_{4-6}$-cycloalkyl group may be replaced by an oxygen or sulphur atom or an —N(R$^{8c}$)— group, where R$^{8c}$ is as defined above,
  with the proviso that such a $C_{3-6}$-cycloalkyl group formed together from R⁴ and R⁵,
    in which one or both methylene groups of the ring which is directly connected to the carbon atom to which the groups R⁴ and R⁵ are attached are replaced by a heteroatom from the group of oxygen, nitrogen and sulphur,
  is excluded
where, unless mentioned otherwise, the term "halogen atom" mentioned above in the definitions means an atom from the group of fluorine, chlorine, bromine and iodine,
where the alkyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different,
and where the hydrogen atoms in the methyl or ethyl groups present in the aforementioned definitions may, unless otherwise mentioned, be wholly or partly replaced by fluorine atoms,
their tautomers, their enantiomers, their diastereomers, their mixtures and their salts.

A 7th embodiment of the present invention encompasses those compounds of the general formula I in which
A is a group of the general formula

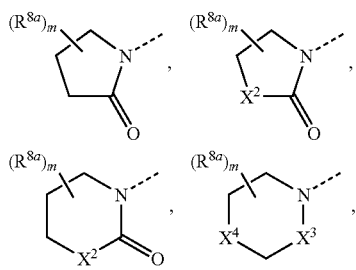

in which
m is the number 1 or 2,
R$^{8a}$ is in each case independently of one another a hydrogen atom or a $C_{1-3}$-alkyl group,
X¹ is a carbonyl group,
X² is an oxygen atom or an —NR$^{8b}$-group,
R$^{8b}$ is a hydrogen atom or a $C_{1-3}$-alkyl group,
X³ is a carbonyl group,
X⁴ is an oxygen atom or an —NR$^{8c}$-group,
R$^{8c}$ is a hydrogen atom or a $C_{1-3}$-alkyl group,
Ar is a phenyl or pyridyl group,
R¹ is a hydrogen, chlorine or bromine atom, a methyl or trifluoromethyl group,
R² is a hydrogen atom,
R³ is a hydrogen atom,
R⁴ is a straight-chain or branched $C_{1-4}$-alkyl group,
  which may optionally be substituted by a hydroxy, a $C_{1-5}$-alkyloxy group, $C_{1-5}$-alkylsulphanyl, $C_{1-5}$-alkylsulphinyl, $C_{1-5}$-alkylsulphonyl, carboxy, $C_{1-5}$-alkyloxycarbonyl, di-($C_{1-5}$-alkyl)-phosphoryl group,
  a heteroaryl-$C_{1-2}$-alkyl or C-linked heteroaryl group, where the heteroaryl group is selected from the group consisting of imidazolyl, furanyl, pyrazolyl, tetrazolyl and pyridinyl,
R⁵ is a hydrogen atom or a methyl group, or
R⁴ and R⁵ together with the carbon atom to which they are bonded form a $C_{3-6}$-cycloalkyl group,
  where one of the methylene groups of a $C_{4-6}$-cycloalkyl group may be replaced by an oxygen or sulphur atom or an —N(R$^{8c}$)— group, where R$^{8c}$ is as defined above,
  with the proviso that such a $C_{3-6}$-cycloalkyl group formed together from R⁴ and R⁵,
    in which one or both methylene groups of the ring which are directly connected to the carbon atom to which the groups R⁴ and R⁵ are attached are replaced by a heteroatom from the group of oxygen, nitrogen and sulphur,
  is excluded,
where the alkyl and alkoxy groups which are present in the aforementioned definitions and which comprise more than two carbon atoms can, unless mentioned otherwise, be straight-chain or branched, and the alkyl groups in the aforementioned dialkylated groups, for example the dialkylamino groups, may be identical or different,
and where the hydrogen atoms of the methyl or ethyl groups present in the aforementioned definitions may, unless mentioned otherwise, be replaced wholly or partly by fluorine atoms,
their tautomers, their enantiomers, their diastereomers, their mixtures and their salts.

An 8th embodiment of the present invention encompasses those compounds of the general formula I according to one of the embodiments 1, 2, 3, 4, 5, 6 or 7 defined above, in which A and the —N(R³)—C(O)—C(R⁴R⁵)—NH—CO— chain in a 6-membered aromatic or heteroaromatic Ar are disposed in the 1,4 position relative to one another and in a 5-membered heteroaromatic Ar are disposed in the 1,3 position relative to one another.

A 9th embodiment of the present invention encompasses those compounds of the general formula I according to one of the embodiments 1, 2, 3, 4, 5, 6, 7 or 8 defined above, in which the group A is the group

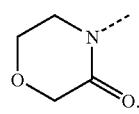

A 10th embodiment of the present invention encompasses those compounds of the general formula I according to one of the embodiments 1, 2, 3, 4, 5, 6, 7, 8 or 9 defined above in which neither R⁴ nor R⁵ is hydrogen.

An 11th embodiment of the present invention encompasses those compounds of the general formula I according to one of the embodiments 1, 2, 3, 4, 5, 6, 7, 8, 9 or 10 defined above in which R⁴ and R⁵ together with the carbon atom to which they are bonded form a cyclic group, where this cyclic group preferably is a $C_{3-8}$-cycloalkyl group, a $C_{3-7}$-cycloalkyl group or a $C_{3-6}$-cycloalkyl group, which in each case is as defined in the 5th, 6th or 7th embodiment.

Examples of preferred compounds of the general formula I which may be mentioned, both as their tautomers, their enantiomers, their diastereomers, their mixtures and their salts, are as follows:

5-ethynyl-N-{1-methyl-1-[3-methyl-4-(3-oxomorpholin-4-yl)phenylcarbamoyl]ethyl}thiophene-2-carboxamide 5-ethynyl-N-{3-[3-methyl-4-(3-oxomorpholin-4-yl)phenylcarbamoyl]tetrahydrofuran-3-yl}thiophene-2-carboxamide 5-ethynyl-N-{2-methoxy-1-[3-methyl-4-(3-oxomorpholin-4-yl)phenylcarbamoyl]ethyl}thiophene-2-carboxamide 5-ethynyl-N-{1-methyl-1-[3-trifluoromethyl-4-(3-oxomorpholin-4-yl)phenylcarbamoyl]ethyl}thiophene-2-carboxamide 5-ethynyl-N-{1-methyl-1-[3-bromo-4-(3-oxomorpholin-4-yl)phenylcarbamoyl]ethyl}thiophene-2-carboxamide 5-ethynyl-N-{1-[3-methyl-4-(3-oxomorpholin-4-yl)phenylcarbamoyl]ethyl}thiophene-2-carboxamide 5-ethynyl-N-{1-[3-methyl-4-(3-oxomorpholin-4-yl)phenylcarbamoyl]butyl}thiophene-2-carboxamide 5-ethynyl-N-{2-methoxy-1-[3-methyl-4-(3-oxomorpholin-4-yl)phenylcarbamoyl]propyl}thiophene-2-carboxamide 5-ethynyl-N-{2-methylsulfanyl-1-[3-methyl-4-(3-oxomorpholin-4-yl)phenylcarbamoyl]ethyl}thiophene-2-carboxamide 5-ethynyl-N-{2-methylsulfinyl-1-[3-methyl-4-(3-oxomorpholin-4-yl)phenylcarbamoyl]ethyl}thiophene-2-carboxamide 5-ethynyl-N-{2-methylsulfonyl-1-[3-methyl-4-(3-oxomorpholin-4-yl)phenylcarbamoyl]ethyl}thiophene-2-carboxamide 5-ethynyl-N-{3-methylsulfanyl-1-[3-methyl-4-(3-oxomorpholin-4-yl)phenylcarbamoyl]propyl}thiophene-2-carboxamide 5-ethynyl-N-{3-methylsulfinyl-1-[3-methyl-4-(3-oxomorpholin-4-yl)phenylcarbamoyl]propyl}thiophene-2-carboxamide 5-ethynyl-N-{3-methylsulfonyl-1-[3-methyl-4-(3-oxomorpholin-4-yl)phenylcarbamoyl]propyl}thiophene-2-carboxamide 5-ethynyl-N-{2-dimethoxyphosphoryl-1-[3-methyl-4-(3-oxomorpholin-4-yl)phenylcarbamoyl]ethyl}thiophene-2-carboxamide 5-ethynyl-N-{3-methoxycarbonyl-1-[3-methyl-4-(3-oxomorpholin-4-yl)phenylcarbamoyl]propyl}thiophene-2-carboxamide 5-ethynyl-N-{3-hydroxycarbonyl-1-[3-methyl-4-(3-oxomorpholin-4-yl)phenylcarbamoyl]propyl}thiophene-2-carboxamide 5-ethynyl-N-{3-(tetrazol-5-yl)-1-[3-methyl-4-(3-oxomorpholin-4-yl)phenylcarbamoyl]propyl}thiophene-2-carboxamide 5-ethynyl-N-{2-phenyl-1-[3-methyl-4-(3-oxomorpholin-4-yl)phenylcarbamoyl]ethyl}thiophene-2-carboxamide 5-ethynyl-N-{2-(pyridin-3-yl)-1-[3-methyl-4-(3-oxomorpholin-4-yl)phenylcarbamoyl]ethyl}thiophene-2-carboxamide 5-ethynyl-N-{1-(pyridin-3-yl)-1-[3-methyl-4-(3-oxomorpholin-4-yl)phenylcarbamoyl]methyl}thiophene-2-carboxamide 5-ethynyl-N-{1-(1H-imidazol-4-yl)-1-[3-methyl-4-(3-oxomorpholin-4-yl)phenylcarbamoyl]methyl}thiophene-2-carboxamide 5-ethynyl-N-{1-(1H-1-methylimidazol-4-yl)-1-[3-methyl-4-(3-oxomorpholin-4-yl)phenylcarbamoyl]methyl}thiophene-2-carboxamide 5-ethynyl-N-{1-(1H-1-methylpyrazol-3-yl)-1-[3-methyl-4-(3-oxomorpholin-4-yl)phenylcarbamoyl]methyl}thiophene-2-carboxamide 5-ethynyl-N-{1-(furan-2-yl)-1-[3-methyl-4-(3-oxomorpholin-4-yl)phenylcarbamoyl]methyl}thiophene-2-carboxamide 5-ethynyl-N-{1-methoxymethyl-1-[3-methyl-4-(3-oxomorpholin-4-yl)phenylcarbamoyl]ethyl}thiophene-2-carboxamide 5-ethynyl-N-{1-methylsulfanylmethyl-1-[3-methyl-4-(3-oxomorpholin-4-yl)phenylcarbamoyl]ethyl}thiophene-2-carboxamide 5-ethynyl-N-{1-trifluoromethyl-1-[3-methyl-4-(3-oxomorpholin-4-yl)phenylcarbamoyl]ethyl}thiophene-2-carboxamide 5-ethynyl-N-{1-methyl-1-[6-fluoro-3-methyl-4-(3-oxomorpholin-4-yl)phenylcarbamoyl]ethyl}thiophene-2-carboxamide 5-ethynyl-N-{1-[3-methyl-4-(3-oxomorpholin-4-yl)phenylcarbamoyl]cyclobut-1-yl}thiophene-2-carboxamide 5-ethynyl-N-{1-[3-methyl-4-(3-oxomorpholin-4-yl)phenylcarbamoyl]cyclopent-1-yl}thiophene-2-carboxamide 5-ethynyl-N-{1-[3-methyl-4-(3-oxomorpholin-4-yl)phenylcarbamoyl]cyclohex-1-yl}thiophene-2-carboxamide 5-ethynyl-N-{3-[4-(3-oxomorpholin-4-yl)phenylcarbamoyl]tetrahydrofuran-3-yl}thiophene-2-carboxamide 5-ethynyl-N-{3-[3-bromo-4-(3-oxomorpholin-4-yl)phenylcarbamoyl]tetrahydrofuran-3-yl}thiophene-2-carboxamide 5-ethynyl-N-{3-[3-methyl-4-(3-oxomorpholin-4-yl)phenylcarbamoyl]oxetan-3-yl}thiophene-2-carboxamide 5-ethynyl-N-{3-[3-methyl-4-(3-oxomorpholin-4-yl)phenylcarbamoyl]thietan-3-yl}thiophene-2-carboxamide 5-ethynyl-N-{3-[3-methyl-4-(3-oxomorpholin-4-yl)phenylcarbamoyl]-1,1-dioxothietan-3-yl}thiophene-2-carboxamide 5-ethynyl-N-{5-[3-methyl-4-(3-oxomorpholin-4-yl)phenylcarbamoyl]-2-oxo-1,3-dioxinane-5-yl}thiophene-2-carboxamide 5-ethynyl-N-{5-[3-methyl-4-(3-oxomorpholin-4-yl)phenylcarbamoyl]-2-oxohexahydropyrimidin-5-yl}thiophene-2-carboxamide 5-ethynyl-N-{3-[3-methyl-4-(3-oxomorpholin-4-yl)phenylcarbamoyl]-5-oxo-pyrrolidin-3-yl}thiophene-2-carboxamide 5-ethynyl-N-{1-methyl-3-[3-methyl-4-(3-oxomorpholin-4-yl)phenylcarbamoyl]-5-oxo-pyrrolidin-3-yl}thiophene-2-carboxamide 5-ethynyl-N-{3-[3-methyl-4-(3-oxomorpholin-4-yl)phenylcarbamoyl]pyrrolidin-3-yl}thiophene-2-carboxamide 5-ethynyl-N-{1-methyl-3-[3-methyl-4-(3-oxomorpholin-4-yl)phenylcarbamoyl]pyrrolidin-3-yl}thiophene-2-carboxamide 5-ethynyl-N-{1-acetyl-3-[3-methyl-4-(3-oxomorpholin-4-yl)phenylcarbamoyl]pyrrolidin-3-yl}thiophene-2-carboxamide 5-ethynyl-N-{3-[3-methyl-4-(3-oxomorpholin-4-yl)phenylcarbamoyl]acetidin-3-yl}thiophene-2-carboxamide 5-ethynyl-N-{3-[5-(3-oxomorpholin-4-yl)pyridyl-2-carbamoyl]tetrahydrofuran-3-yl}thiophene-2-carboxamide 5-ethynyl-N-{3-[3-methyl-4-(2-oxopyrrolidin-1-yl)phenylcarbamoyl]tetrahydrofuran-3-yl}thiophene-2-carboxamide 5-ethynyl-N-{3-[3-methyl-4-(2-oxo-5-methylpyrrolidin-1-yl)phenylcarbamoyl]tetrahydrofuran-3-yl}thiophene-2-carboxamide 5-ethynyl-N-{3-[3-methyl-4-(2-oxo-4-methyloxazolidin-3-yl)phenylcarbamoyl]tetrahydrofuran-3-yl}thiophene-2-carboxamide 5-ethynyl-N-{3-[3-methyl-4-(2-oxo-4,4-dimethyloxazolidin-3-yl)phenylcarbamoyl]tetrahydrofuran-3-yl}thiophene-2-carboxamide 5-ethynyl-N-{3-[3-methyl-4-(2-oxo-5,5-dimethylpyrrolidin-1-yl)phenylcarbamoyl]tetrahydrofuran-3-yl}thiophene-2-carboxamide 5-ethynyl-N-{3-[3-methyl-4-(2-oxooxazolidin-3-yl)phenylcarbamoyl]-tetrahydrofuran-3-yl}thiophene-2-carboxamide 5-ethynyl-N-{3-[3-methyl-4-(2-oxoimidazolidin-1-yl)phenylcarbamoyl]tetrahydrofuran-3-yl}thiophene-2-carboxamide 5-ethynyl-N-{3-[3-methyl-4-(3-methyl-2-oxoimidazolidin-1-yl)phenylcarbamoyl]tetrahydrofuran-3-yl}thiophene-2-carboxamide 5-ethynyl-N-{1-methyl-1-[3-methyl-4-(2-oxopiperidin-1-yl)phenylcarbamoyl]ethyl}thiophene-2-carboxamide 5-ethynyl-N-{1-methyl-1-[3-methyl-4-(2-oxoperhydro-1,3-oxazin-3-yl)phenylcarbamoyl]ethyl}thiophene-2-carboxamide 5-ethynyl-N-{1-methyl-1-[3-methyl-4-(2-oxotetrahydropyrimidin-1-yl)phenylcarbamoyl]ethyl}thiophene-2-carboxamide 5-ethynyl-N-{1-methyl-1-[3-methyl-4-(2-oxopiperazin-1-yl)phenylcarbamoyl]ethyl}thiophene-2-carboxamide 5-ethynyl-N-{1-methyl-1-[3-methyl-4-(2-oxo-4-methylpiperazin-1-yl)phenylcarbamoyl]ethyl}thiophene-2-carboxamide 5-ethynyl-N-{1-methyl-1-[3-methyl-4-(1,1-dioxoperhydro-1,2-thiazin-2-yl)phenylcarbamoyl]ethyl}thiophene-2-carboxamide 5-ethynyl-N-{1-methyl-1-[3-methyl-4-(2-iminopiperidin-1-yl)phenylcarbamoyl]ethyl}thiophene-2-carboxamide 5-ethynyl-N-{1-methyl-1-

[3-methyl-4-(3-iminomorpholin-4-yl)phenylcarbamoyl]
ethyl}thiophene-2-carboxamide
5-ethynyl-N-{1-methyl-1-[3-methyl-4-(2-iminoperhydroazepin-1-yl)phenylcarbamoyl]ethyl}thiophene-2-carboxamide 5-ethynyl-N-{1-methyl-1-[3-methyl-4-(5-oxoperhydro-1,4-oxazepin-4-yl)phenylcarbamoyl]ethyl}thiophene-2-carboxamide 5-ethynyl-N-{1-methyl-1-[3-methyl-4-(2-oxoperhydro-1,3-oxazepin-3-yl)phenylcarbamoyl]ethyl}thiophene-2-carboxamide
5-ethynyl-N-{1-[3-chloro-4-(5-cyaniminoperhydro-1,4-oxazepin-4-yl)phenylcarbamoyl]ethyl}thiophene-2-carboxamide 5-ethynyl-N-{1-[3-methyl-4-(5-hydroxyiminoperhydro-1,4-oxazepin-4-yl)phenylcarbamoyl]ethyl}thiophene-2-carboxamide The invention also relates to physiologically acceptable salts of the compounds according to the embodiments and examples defined above.

The invention also relates to medicaments comprising a compound or a physiologically acceptable salt of a compound according to the embodiments and examples defined above, optionally in addition to one or more inert carriers and/or diluents.

The invention also relates to the use of a compound or a physiologically acceptable salt of a compound according to the embodiments and examples defined above for the preparation of a medicament having an inhibitory effect on factor Xa and/or an inhibitory effect on the related serine proteases.

The invention also relates to a process for producing a medicament, characterized in that a compound or a physiologically acceptable salt of a compound according to the embodiments and examples defined above is incorporated by non-chemical means into one or more inert carriers and/or diluents.

The compounds of the general formula I are obtained according to the invention by processes known per se, for example by the following processes:
(a) To prepare a compound of the general formula

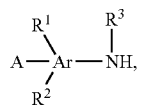
(II)

in which A and $R^1$ to $R^3$ are defined as mentioned in embodiment 1:
1) Preparation of a compound of the general formula (II) in which $R^3$ is a hydrogen atom, and A, $R^1$ and $R^2$ are defined as mentioned in embodiment 1:
i) reduction of the nitro group of a compound of the general formula (III)

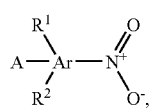
(III)

in which A, $R^1$ and $R^2$ are defined as mentioned in embodiment 1:

The reduction of the nitro group is carried out for example preferably in a solvent or solvent mixture such as water, aqueous ammonium chloride solution, hydrochloric acid, sulphuric acid, phosphoric acid, formic acid, acetic acid, acetic anhydride with base metals such as iron, zinc, tin or sulphur compounds such as ammonium sulphide, sodium sulphide or sodium dithionite or by catalytic hydrogenation with hydrogen, for example under a pressure of between 0.5 and 100 bar, but preferably between 1 and 50 bar, or with hydrazine as reducing agent, preferably in the presence of a catalyst such as, for example, Raney nickel, palladium/carbon, platinum oxide, platinum on mineral fibre or rhodium, or with complex hydrides such as lithium aluminium hydride, sodium borohydride, sodium cyanoborohydride, diisobutylaluminium hydride, preferably in a solvent or solvent mixture such as water, methanol, ethanol, isopropanol, pentane, hexane, cyclohexane, heptane, benzene, toluene, xylene, ethyl acetate, methyl propionate, glycol, glycol dimethyl ether, diethylene glycol dimethyl ether, dioxane, tetrahydrofuran, N-methylpyrrolidinone, or else N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C.

The compounds of the general formula (III) can be obtained as follows:
a) Selective oxidation of compounds of the general formula (IV):

(IV)

in which A' is a substituted cycloalkylenimino group which optionally comprises further heteroatoms, and $R^1$ and $R^2$ are defined as mentioned in embodiment 1:

The oxidation of a methylene group adjacent to the nitrogen is carried out for example with oxidizing agents such as potassium permanganate, potassium chromate, potassium dichromate, chromium(VI) oxide, mercury(II) chloride, selenium(IV) oxide, lead(IV) oxide, lead(II,IV) oxide, potassium peroxomonosulphate, hydrogen peroxide, sodium hypochlorite, where appropriate in the presence of a suitable catalyst such as nickel(II) chloride, cobalt(II) chloride, ruthenium(III) chloride, osmium(VIII) oxide, vanadium(IV) oxide and/or in the presence of a crown ether such as 18-crown-6, in a solvent or solvent mixture such as water, formic acid, acetic acid, ethyl acetate, benzene, pyridine, dichloromethane, chloroform, tetrachloromethane, optionally under 2-phase conditions in the presence of a suitable phase-transfer catalyst such as, for example, tetrabutylammonium chloride, tetrabutylammonium bromide, benzyltriethylammonium chloride or methyltrioctylammonium chloride, optionally in the presence of an acid such as acetic acid, hydrochloric acid, hydrobromic acid, sulphuric acid, phosphoric acid, sodium hydrogensulphate, sodium dihydrogenphosphate and/or a base such as sodium hydroxide, potassium hydroxide, ammonia, pyridine, potassium phosphate, dipotassium hydrogenphosphate or sodium acetate at temperatures between −30 and 250° C., but preferably between 0 and 150° C. This reaction can be carried out for example as described by J. H. Markgraf, C. A. Stickney, J. *Heterocycl. Chem.* 2000, 37(1), 109.

The compounds of the general formula (IV) can be obtained as follows:
a)i) Nucleophilic substitution with a compound of the general formula

A'-H (V), in which A' is a cycloalkylenimino group optionally comprising further heteroatoms, on the aromatic compound of the general formula

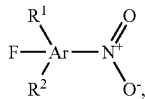

(VI)

in which $R^1$ and $R^2$ are defined as mentioned in embodiment 1.

The nucleophilic substitution is preferably carried out in a solvent or solvent mixture such as ethanol, isopropanol, benzene, chlorobenzene, toluene, xylene, glycol, glycol dimethyl ether, diethylene glycol dimethyl ether, dimethylformamide, N-methylpyrrolidinone, tetralin, dimethyl sulphoxide, sulpholane, methylene chloride, chloroform, tetrachloromethane or else N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., where appropriate preferably in the presence of bases such as potassium carbonate, sodium carbonate, potassium tert-butoxide, sodium ethanolate, potassium hexamethyldisilazane, sodium hydride or lithium diisopropylamide.

a)ii) Transition metal-catalysed coupling reaction of a compound of the general formula

A'-H  (V)

in which A' is a cycloalkylenimino group optionally comprising further heteroatoms, on the aromatic compound of the general formula

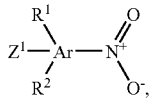

(VII)

in which $R^1$ and $R^2$ are defined as mentioned in embodiment 1, and $Z^1$ is a chlorine, bromine or iodine atom or a triflate group.

The reaction is preferably carried out in a solvent or solvent mixture such as benzene, toluene, xylene, tetrahydrofuran, dioxane, diethyl ether, tert-butyl methyl ether, ethylene glycol dimethyl ether, diethylene glycol dimethyl ether, sulpholane, dimethylformamide, N-methylpyrrolidinone, tetralin, dimethyl sulphoxide, methylene chloride, chloroform or tetrachloromethane, for example at temperatures between −30 and 250° C., but preferably between 0 and 150° C., preferably in the presence of transition metal catalysts such as nickel on activated carbon, palladium/carbon, tetrakis(triphenylphosphine)palladium(0), tris(dibenzylideneacetone)dipalladium(0), palladium(II) acetate, palladium(II) chloride, bis(triphenylphoshine)palladium(II) chloride, bis(tricyclohexylphosphine)-palladium(II) chloride, bis(triethylphosphine)palladium(II) chloride, bis(tri-o-tolylphosphine)palladium(II) chloride, optionally in the presence of ligands such as triphenylphosphine, tri-o-tolylphosphine, tri-tert-butylphosphine, 1,3-bis(diphenylphosphino)propane, 2,2'-bis(diphenylphosphino)-1,1'-dinaphthyl, 1,1'-bis(diphenylphosphino)ferrocene, xantphos, and preferably in the presence of a base such as sodium methanolate, sodium ethanolate, sodium tert-butoxide, potassium tert-butoxide, sodium tert-butyldimethylsilanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6 ether and preferably with use of an inert gas atmosphere (for example nitrogen or argon) and optionally under pressure.

b) Acylation/sulphonylation and alkylation of a compound of the general formula

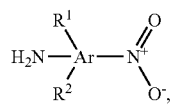

(VIII)

in which $R^1$ and $R^2$ are defined as mentioned in embodiment 1, with a compound of the general formula

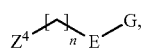

(IX)

in which E is a carbonyl, oxycarbonyl, sulphonyl group or a sulphamoyl group optionally substituted on the nitrogen atom as mentioned in embodiment 1, G is a chlorine, bromine or iodine atom or an anhydride, $C_{1-5}$-alkoxy or benzotriazoloxy group or E and G together are an isocyanato or cyano group and $Z^4$ is a nucleofugic leaving group, for example a chlorine, bromine or iodine atom, a tosylate, triflate or mesylate group, and n is a number between 2 and 5, where individual methylene groups may be additionally substituted or replaced by heteroatoms in accordance with the description mentioned in embodiment 1, and subsequent intramolecular cyclization by alkylation of the anilide nitrogen with elimination of the nucleofugic leaving group $Z^4$.

The acylation/sulphonylation is preferably carried out in a solvent or solvent mixture such as benzene, chlorobenzene, toluene, xylene, glycol dimethyl ether, diethylene glycol dimethyl ether, dimethylformamide, N-methylpyrrolidinone, tetralin, dimethyl sulphoxide, sulpholane, methylene chloride, chloroform, tetrachloromethane, N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., preferably in the presence of bases such as pyridine, triethylamine, p-dimethylaminopyridine, potassium carbonate, sodium carbonate, potassium tert-butoxide, sodium methanolate, sodium ethanolate or basic ion exchanger.

The subsequent intramolecular alkylation is preferably carried out in a solvent or a solvent mixture such as benzene, chlorobenzene, toluene, xylene, glycol dimethyl ether, diethylene glycol dimethyl ether, dimethylformamide, dimethyl sulphoxide, sulpholane, methylene chloride, tetrachloromethane, N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., preferably in the presence of bases such as pyridine, triethylamine, potassium carbonate, sodium carbonate, potassium tert-butoxide, sodium methanolate, sodium ethanolate, sodium hydride, potassium hexamethyldisilazane or lithium diisopropylamide.

c) Nucleophilic substitution with a compound of the general formula

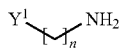 (X)

in which $Y^1$ is a hydroxyl, amino or thiol function which is optionally blocked by an appropriate protecting group, and n is a number between 0 and 4, on the aromatic compound of the general formula

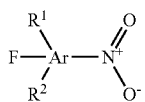 (VI)

in which $R^1$ and $R^2$ are defined as mentioned in embodiment 1, and subsequent ring closure by reaction with a compound of the general formula

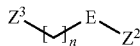 (XI)

in which $Z^2$ and $Z^3$ are nucleofugic leaving groups such as chlorine, bromine or iodine atoms or triflate, mesylate or tosylate groups, E is a carbonyl or sulphonyl group, and n is a number between 0 and 4, where individual methylene groups may be substituted or replaced by optionally substituted heteroatoms or other groups in accordance with the description in embodiment 1.

The initial nucleophilic aromatic substitution is carried out for example as described under (a) 1) i) a)i). It is followed where appropriate by deblocking of the nucleophilic group $Y^1$ by processes known from the literature or as described generally hereinafter.

Reaction of the compound resulting therefrom with the compound of the general formula (X) is preferably carried out in a solvent or solvent mixture such as benzene, chlorobenzene, toluene, xylene, glycol dimethyl ether, diethylene glycol dimethyl ether, dimethylformamide, N-dimethylpyrrolidinone, tetralin, dimethyl sulphoxide, sulpholane, methylene chloride, chloroform, tetrachloromethane, N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., preferably in the presence of bases such as pyridine, triethylamine, p-dimethylaminopyridine, potassium carbonate, sodium carbonate, potassium tert-butoxide, sodium methanolate, sodium ethanolate or basic ion exchanger.

d) Alkylation and subsequent acylation/sulphonylation of a compound of the general formula

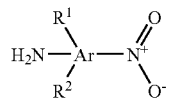 (VIII)

in which $R^1$ and $R^2$ are defined as mentioned in embodiment 1, with a compound of the general formula

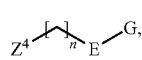 (IX)

in which E is a carbonyl, oxycarbonyl, sulphonyl group or a sulphamoyl group optionally substituted on the nitrogen atom as mentioned in embodiment 1, G is a chlorine, bromine or iodine atom or an anhydride, $C_{1-5}$-alkoxy or benzotriazoloxy group or E and G together are an isocyano group and $Z^4$ is a nucleofugic leaving group, for example a chlorine, bromine or iodine atom, a tosylate, triflate or mesylate group, and n is a number between 2 and 5, where individual methylene groups may be additionally substituted or replaced by heteroatoms in accordance with the description mentioned in embodiment 1, and subsequent intramolecular cyclization by alkylation of the anilide nitrogen with elimination of the nucleofugic leaving group $Z^4$.

The alkylation is preferably carried out in a solvent or solvent mixture such as benzene, chlorobenzene, toluene, xylene, glycol dimethyl ether, diethylene glycol dimethyl ether, dimethylformamide, dimethyl sulphoxide, sulpholane, methylene chloride, tetrachloromethane, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., preferably in the presence of bases such as pyridine, triethylamine, potassium carbonate, sodium carbonate, potassium tert-butoxide, sodium methanolate, sodium ethanolate, sodium hydride, potassium hexamethyldisilazane or lithium diisopropylamide.

The subsequent intramolecular acylation/sulphonylation is preferably carried out in a solvent or solvent mixture such as benzene, chlorobenzene, toluene, xylene, glycol dimethyl ether, diethylene glycol dimethyl ether, dimethylformamide, N-methylpyrrolidinone, tetralin, dimethyl sulphoxide, sulpholane, methylene chloride, chloroform, tetrachloromethane, N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., preferably in the presence of bases such as pyridine, triethylamine, p-dimethyl-aminopyridine, potassium carbonate, sodium carbonate, potassium tert-butoxide, sodium methanolate, sodium ethanolate or basic ion exchanger.

e) Sequential alkylation of a compound of the general formula

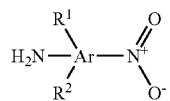 (VIII)

in which $R^1$ and $R^2$ are defined as mentioned in embodiment 1, with a compound of the general formula

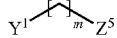 (XII)

in which $Z^5$ is a nucleofugic leaving group such as, for example, a bromine or chlorine atom or a tosylate, triflate or mesylate group, $Y^1$ is a nucleophilic group, which is optionally blocked by a suitable protecting group, such as a hydroxy group or an amino group which is optionally substituted as described above, and m is a number between 2 and 5, where individual methylene groups may additionally be substituted or replaced by heteroatoms in accordance with the description mentioned in embodiment 1, with subsequent acylation/sulphonylation with a compound of the general formula

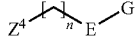 (IX)

in which E is a carbonyl, oxycarbonyl, sulphonyl group or a sulphamoyl group which is optionally substituted on the nitrogen atom as mentioned in embodiment 1, G is a chlorine, bromine or iodine atom or an anhydride, $C_{1-5}$-alkoxy or benzotriazoloxy group or E and G together are an isocyanato or cyano group and $Z^4$ is a nucleofugic group, for example a bromine or chlorine atom, a tosylate, triflate or mesylate group, and n is a number between 2 and 5, where individual methylene groups may be additionally substituted or replaced by heteroatoms in accordance with the description mentioned in embodiment 1, and subsequent intramolecular cyclization by alkylation of the nucleophilic group $Y^1$ which, where appropriate, hias been previously deblocked with elimination of the nucleofugic leaving group $Z^4$.

Both the necessary alkylations and the acylation/sulphonylation can be carried out in analogy to the conditions described under (a) 1) i) b) or (a) 1) i) d).

f) Carbamoylation/urea formation with a compound of the general formula

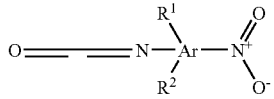 (XIII)

in which $R^1$ and $R^2$ are defined as mentioned in embodiment 1, and which can be obtained from compounds of the general formula (VIII) by processes known from the literature, for example by reaction with phosgene in toluene, with a compound of the general formula

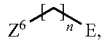 (XIV)

in which $Z^6$ is a nucleofugic leaving group, for example a chlorine, bromine or iodine atom, a tosylate, triflate or mesylate group, and E is a hydroxyl, amino or $C_{1-3}$-alkylamino function, and n is a number between 2 and 4, where individual methylene groups may additionally be substituted in accordance with the description mentioned in embodiment 1, and subsequent intramolecular cyclization by alkylation of the anilide nitrogen with elimination of the nucleofugic leaving group $Z^6$.

The carbamoylation is preferably carried out in a solvent or solvent mixture such as benzene, chlorobenzene, toluene, xylene, glycol dimethyl ether, diethylene glycol dimethyl ether, dimethylformamide, N-methylyrrolidinone, tetralin, dimethyl sulphoxide, sulpholane, methylene chloride, chloroform, tetrachloromethane, N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C.

The subsequent intramolecular alkylation is carried out for example in analogy to the description under (a) 1) i) b).

ii) Transition metal-catalysed coupling reaction of a compound of the general formula

A-H (XV), in which A is defined as mentioned in embodiment 1, with the aromatic compound of the general formula

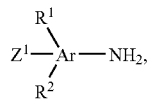 (XVI)

in which $R^1$ and $R^2$ are defined as mentioned in embodiment 1, and $Z^1$ is a chlorine, bromine or iodine atom or a triflate group.

The reaction is preferably carried out in a solvent or solvent mixture such as benzene, toluene, xylene, tetrahydrofuran, dioxane, diethyl ether, tert-butyl methyl ether, ethylene glycol dimethyl ether, diethylene glycol dimethyl ether, sulpholane, dimethylformamide, N-methylpyrrolidinone, tetralin, dimethyl sulphoxide, methylene chloride, chloroform or tetrachloromethane, for example at temperatures between −30 and 250° C., but preferably between 0 and 200° C., preferably in the presence of transition metal catalysts such as tetrakis(triphenylphoshine)palladium(0), tris(dibenzylideneacetone)dipalladium(0), palladium(II) acetate, palladium (II) chloride, bis(triphenylphoshine)palladium(II) chloride, bis(tricyclohexylphosphine)palladium(II) chloride, bis(triethylphosphine)-palladium(II) chloride, bis(tri-o-tolylphosphine)palladium(II) chloride, optionally in the presence of ligands such as triphenylphosphine, tri-o-tolylphosphine, tri-tert-butylphosphine, 1,3-bis(diphenylphosphino)propane, 2,2'-bis(diphenylphosphino)-1,1'-dinaphthyl, 1,1'-bis(diphenylphosphino)-ferrocene, xantphos, or for example in the presence of a transition metal catalyst such as copper(I) iodide, copper(I) bromide or copper(I) acetate and preferably in the presence of a base such as tetramethylguanidine, tetramethylethylenediamine or N,N'-dimethylenediamine and preferably in the presence of a base such as sodium methanolate, scidium ethanolate, sodium tert-butoxide, potassium tert-butoxide, sodium tert-butyldimethyl-silanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6 ether and preferably with use of an inert gas atmosphere (for example nitrogen or argon) and optionally under pressure.

2) Preparation of a compound of the general formula (II) in which $R^3$ is a $C_{1-3}$-alkyl group, and A and $R^1$ to $R^3$ are defined as mentioned in embodiment 1:

Reductive amination of a compound of the general formula (II) in which $R^3$ is a hydrogen atom, and A and $R^1$ to $R^3$ are defined as mentioned in embodiment 1:

The reaction with the appropriate $R^3$-aldehyde (formaldehyde or paraformaldehyde for $R^3$ methyl, acetaldehyde or paraldehyde for $R^3$ ethyl, propionaldehyde for $R^3$ propyl) is preferably carried out in a solvent or solvent mixture such as methanol, ethanol, propanol, isopropanol, butanol, tetrahydrofuran, dioxane, diethyl ether, tert-butyl methyl ether, ethylene glycol dimethyl ether, diethylene glycol dimethyl ether, sulpholane, dimethylformamide, N-methylpyrrolidinone, tetralin, dimethyl sulphoxide, methylene chloride, chloroform or tetrachloromethane, for example at temperatures between −30 and 250° C., but preferably between −10 and 150° C., optionally in the presence of a base such as sodium methanolate, sodium ethanolate, sodium tert-butoxide, potassium tert-butoxide, sodium tert-butyldimethylsilanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6 ether, followed by reduction of the resulting imide by hydrogenation with hydrogen, for example under a pressure of between 0.5 and 100 bar, but preferably between 1 and 50 bar, expediently in the presence of a catalyst such as, for example, Raney nickel, palladium/carbon, platinum oxide, platinum on mineral fibre or rhodium, or with complex hydrides such as lithium aluminium hydride, sodium borohydride, sodium cyanoborohydride, diisobutylaluminium hydride, for example at temperatures between −30 and 250° C., but preferably between 0 and 150° C.

3) Preparation of a compound of the general formula (II) in which $R^1$ to $R^3$ are defined as in embodiment 1, and which comprise, according to the definition of A, thiocarbonyl groups or optionally appropriately substituted imino groups in the ring:

i) Thionylation of the appropriate carbonyl-analogous compound of the general formula (XV), optionally with subsequent alkylation of the sulphur and reaction with an appropriately substituted amine (for example methylamine, hydroxylamine, acetoxyamine, methoxyamine, cyanamide or corresponding analogous compounds), and subsequent coupling of the resulting compound with a compound of the general formula (XVI) according to the description of (a) 1) ii)

The thionylation is preferably carried out for example in a solvent or solvent mixture such as pentane, hexane, cyclohexane, heptane, benzene, toluene, xylene, glycol dimethyl ether, diethylene glycol dimethyl ether, dioxane, tetrahydrofuran, dichloromethane, chloroform, tetrachloromethane, 1,2-dichloroethane, N-methylpyrrolidinone, or else N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, with reagents such as, for example, phosphorus pentasulphide, 2,2-bis(4-methoxyphenyl)-1,3,2,4-dithiadiphosphetane 2,4-disulphide (Lawesson's reagent) or reagent mixtures such as, for example, phosphorus oxychloride followed by 1,1,1,3,3,3-hexamethyldisilathiane, trifluorosulphonic anhydride followed by hydrogen sulphide, or the mixture of hydrogen sulphide, chlorotrimethylsilane and lithium diisopropylamide, optionally in the presence of a base such as potassium carbonate, sodium carbonate, sodium bicarbonate, pyridine, triethylamine, for example at temperatures between −30 and 250° C., but preferably between −10 and 150° C. Any subsequent alkylation of the appropriate thiocarbonyl compounds is preferably carried out for example in a solvent or solvent mixture such as pentane, hexane, cyclohexane, heptane, benzene, toluene, xylene, glycol dimethyl ether, diethylene glycol dimethyl ether, dioxane, tetrahydrofuran, dichloromethane, chloroform, tetrachloromethane, 1,2-dichloroethane, chlorobenzene, pyridine, water, methanol, ethanol, n-propanol, isopropanol, n-butanol, acetone, butanone, acetonitrile or nitromethane, where appropriate under 2-phase conditions with addition of a phase-transfer catalyst such as tetrabutylammonium chloride, tetrabutylammonium bromide, methyltrioctylammonium chloride or Aliquat 336 with reagents such as, for example, methyl iodide, ethyl bromide, dimethyl sulphate, diethyl sulphate or trimethyloxonium tetrafluoroborate, preferably where appropriate in the presence of a base such as potassium carbonate, sodium carbonate, sodium bicarbonate, pyridine, triethylamine, N-ethyldiisopropylamine, N—$C_{1-5}$-alkylmorpholine, N—$C_{1-5}$-alkylpiperidine, N—$C_{1-5}$-alkylpyrrolidine, for example at temperatures between −30 and 250° C., but preferably between −10 and 150° C. The reaction, following an alkylation, with an amino compound to prepare the corresponding imine is preferably carried out for example in a solvent or solvent mixture such as pentane, hexane, cyclohexane, heptane, benzene, toluene, xylene, glycol dimethyl ether, diethylene glycol dimethyl ether, dioxane, tetrahydrofuran, dichloromethane, chloroform, tetrachloromethane, 1,2-dichloroethane, chlorobenzene, pyridine, water, methanol, ethanol, n-propanol, isopropanol, n-butanol, acetone, butanone, acetonitrile or nitromethane, with appropriate reagents depending on the substitution of the imine, such as, for example, ammonia, sodamide, hydroxylamine, methoxyamine, ethoxyamine, propoxyamine, acetoxyamine or cyanamide, optionally in the presence of a base such as sodium hydride, potassium hydride, potassium carbonate, sodium carbonate, sodium bicarbonate, pyridine, triethylamine and optionally under pressure, for example at temperatures between −30 and 250° C., but preferably between −20 and 120° C.

ii) Thionylation of the appropriate carbonyl-analogous compound of the general formula (III), which can be obtained by the processes described under (a) 1) i) a), b), c), d) and e), optionally with subsequent alkylation of the sulphur and reaction with an appropriately substituted amine (for example methylamine, hydroxylamine, acetoxyamine, methoxyamine, cyanamide or corresponding analogous compounds), and subsequent reduction of the nitro group by the processes described under (a) 1) i), optionally with subsequent reductive amination by processes described under (a) 2).

The thionylation and, where appropriate, subsequent reaction for the alkylation and imine formation can be carried out analogously to the processes described under (a) 3) i).

iii) Thionylation of the appropriate carbonyl-analogous compound of the general formula (II), which can be obtained by the processes described under (a) 1) i), ii), iii) and (a) 2), optionally with subsequent alkylation of the sulphur and reaction with an appropriately substituted amine (for example methylamine, hydroxylamine, acetoxyamine, methoxyamine, cyanamide or corresponding analogous compounds), where the anilinic amino group which is present is, in any subsequent alkylation, preferably blocked by suitable protecting groups which are eliminated after reaction to give the imine.

The thionylation and where appropriate the subsequent reaction for alkylation and imine formation can be carried out analogously to the processes described under (a) 3) i).

4) Preparation of a compound of the general formula (II) in which $R^1$ to $R^3$ are defined as mentioned in embodiment 1, and which optionally comprise, according to the definition of A, appropriately substituted imino groups in the ring:
i) alkylation of the carbonyl-analogous compounds of the general formula (XV) and subsequent reaction with an appropriately substituted amine (for example methylamine, hydroxylamine, acetoxyamine, methoxyamine, cyanamide or corresponding analogous compounds), and subsequent coupling of the resulting compound with a compound of the general formula (XVI) according to the description of (a) 1) ii)

The alkylation and the following reaction with an amino compound to prepare the corresponding imine can be carried out as described under (a) 3) i).

ii) Alkylation of the carbonyl-analogous compounds of the general formula (III), which can be obtained by the processes described under (a) 1) i) a), b), c), d) and e), and subsequent reaction with an appropriately substituted amine (for example methylamine, hydroxylamine, acetoxyamine, methoxyamine, cyanamide or corresponding analogous compounds), and subsequent reduction of the nitro group by the processes described under (a) 1) i), where appropriate with subsequent reductive amination by processes described under (a) 2).

The alkylation and the following reaction with an amino compound to prepare the corresponding imine can be carried out as described under (a) 3) i).

5) A compound of the general formula (II) in which $R^3$ is a hydrogen atom, and A, $R^1$ and $R^2$ are defined as mentioned in embodiment 1, can, however, also be prepared in analogy to the synthetic strategies described in WO 2004/76429 and in WO 2004/65369.

(b) Preparation of a compound of the general formula

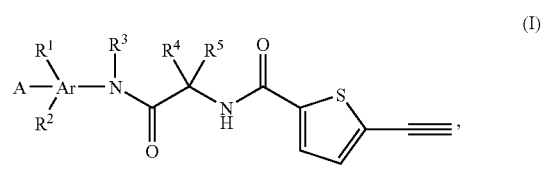

in which A, Ar and $R^1$ to $R^5$ are defined as mentioned in embodiment 1, can be prepared from 11 for example according to one of the following formula schemes 1 and 2:

Scheme 1

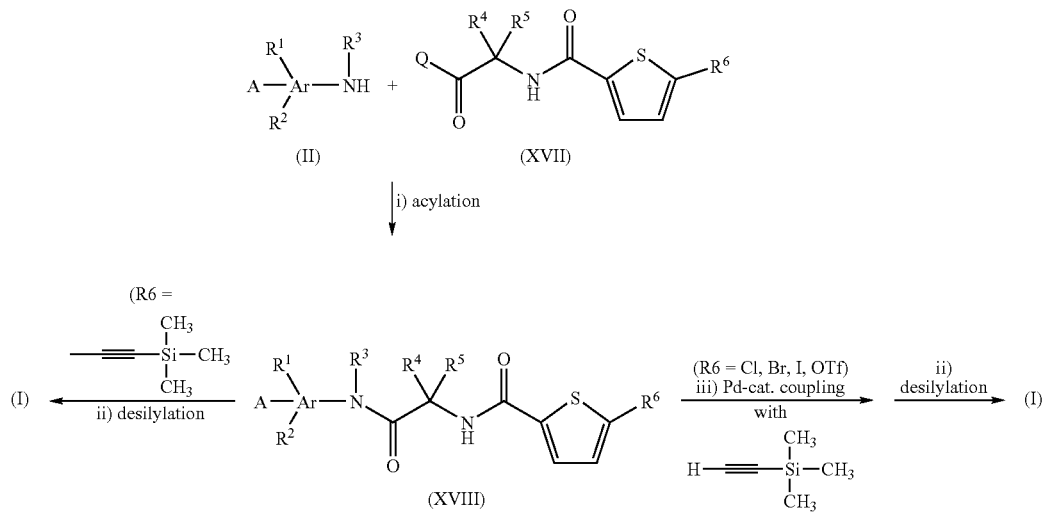

Scheme 2

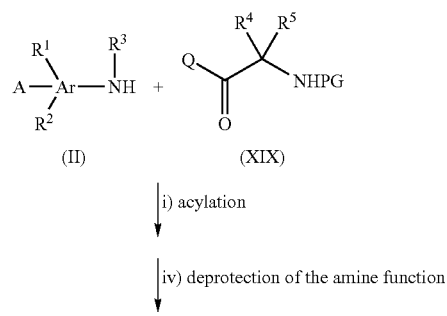

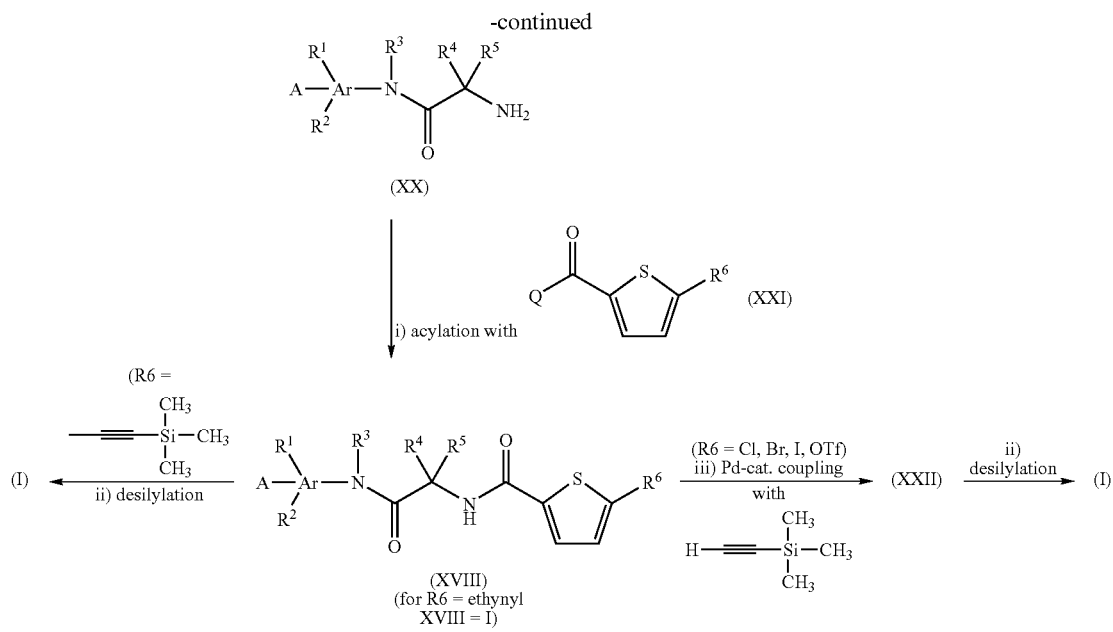

where

R⁶ is a chlorine, bromine or iodine atom or a trifluoromethanesulphonyl, trimethylsilylethynyl or an ethynyl group, and Q is a hydroxy or $C_{1-4}$-alkoxy group, a halogen atom or an alkoxycarbonyloxy or acyloxy group, and PG is a hydrogen atom or a protecting group for the amino function known from the literature, such as, for example, a tert-butoxycarbonyl, benzyloxycarbonyl or a trifluoroacetyl group.

Reaction stages i)-iv) described in scheme 1 and 2 can be carried out in the manner described in the examples or under conditions known from the literature, for example:

i) Acylation of an Amine (II) or (XX) with an Optionally Activated Carboxylic Acid (XVII) or (XIX) or (XXI)

The acylation is preferably carried out with an appropriate halide or anhydride in a solvent such as methylene chloride, chloroform, carbon tetrachloride, ether, tetrahydrofuran, dioxane, benzene, toluene, acetonitrile, dimethylformamide, sodium hydroxide solution or sulpholane, where appropriate in the presence of an inorganic or organic base at temperatures between −20 and 200° C., but preferably at temperatures between −10 and 160° C.

The acylation can, however, also be carried out with the free acid, where appropriate in the presence of an agent activating the acid or of a dehydrating agent, for example in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexyl-carbodiimide/camphorsulphonic acid (in analogy to Helvetica Chimica Acta 1986, 1153), N,N'-dicyclohexylcarbodiimide/N-hydroxysuccinimide or 1-hydroxybenztriazole, N,N'-carbonyldiimidazole, O-(benzotriazol-1-yl)-N,N,N',N'-tetramethyluronium tetrafluoroborate/N-methylmorpholine, O-(benzotriazol-1-yl)-N,N,N',N'-tetramethyluronium tetrafluoroborate/N-ethyldiisopropylamine, O-pentafluorophenyl-N,N,N',N'-tetramethyluronium hexafluorophosphate/triethylamine, N,N'-thionyldiimidazole or triphenylphosphine/carbon tetrachloride, at temperatures between −20 and 200° C., but preferably at temperatures between −10 and 160° C.

The acylation can, however, also be carried out in a solvent or solvent mixture such as dichloromethane, trichloromethane, benzene, chlorobenzene, toluene, xylene, hexamethyldisiloxane, acetonitrile, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, in the presence of 4-trifluoromethylbenzoic anhydride, silver triflate and titanium(IV) chloride, preferably in the presence of a dehydrating agent such as molecular sieves, sodium sulphate, magnesium sulphate, or in the presence of 4-trifluoromethylbenzoic anhydride and ytterbium(III) triflate, it also being possible to add water to the solvent mixture, for example at temperatures between −30 and 250° C., but preferably between 0 and 150° C. (I. Shiina, M. Miyashita, M. Nagai, T. Mukaiyama, *Heterocycles* 1995, 40 (1), 141-148).

Further processes for amide coupling are described for example in P. D. Bailey, I. D. Collier, K. M. Morgan in "Comprehensive Functional Group Interconversions", Vol. 5, pages 257 et seq., Pergamon 1995.

ii) Desilylation of a Silylated Ethynyl Compound (XVIII) or (XXII)

Elimination of a trimethylsilyl group takes place for example in water, an aqueous solvent mixture or a lower alcohol such as methanol or ethanol in the presence of a base such as lithium hydroxide, sodium hydroxide, potassium carbonate or sodium methoxide. For elimination in organic solvents such as, for example, diethyl ether, tetrahydrofuran, dimethylformamide or dichloromethane, fluoride reagents are also suitable, such as, for example, tetrabutylammonium fluoride or potassium fluoride.

iii) Palladium-Catalysed Coupling of Trimethylacetylene with a Compound (XVIII) in which R⁶ is a Chlorine, Bromine or Iodine Atom or a Trifluoromethylsulphonyl Group:

The reaction is preferably carried out in a solvent such as acetonitrile, diethyl ether, tetrahydrofuran or dimethylformamide or a solvent mixture in the presence of a palladium catalyst such as, for example, bis(triphenylphosphine)palladium(II) choride, palladium(II)-[1,1'-bis(diphenylphosphino)ferrocene]chloride or tetrakis(triphenylphosphine)-palladium(0) in the presence of a tertiary or inorganic base such as triethylamine, N-isopropyldiethylamine, potassium tert-butoxide, sodium carbonate or caesium carbonate and in the presence of a reaction promoter such as a copper halide such as copper(I) iodide and at temperatures between 20 and 120° C., preferably at temperatures between 20 and 90° C. under an argon or nitrogen atmosphere (see also K. Sonogashira, Comprehensive Organic Synthesis, Vol. 3, page 52 et seq., Pergamon Press, Oxford 1991).

iv) Elimination of an Amino Protecting Group

Where appropriate the subsequent elimination of a protecting group used takes place for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether cleavage, e.g. in the presence of iodotrimethylsilane, at temperatures between 0 and 100° C., preferably at temperatures between 10 and 50° C.

However, elimination of a benzyl, methoxybenzyl or benzyloxycarbonyl group takes place for example by hydrogenolysis, e.g. with hydrogen in the presence of a catalyst such as palladium/carbon in a solvent such as methanol, ethanol, ethyl acetate, dimethylformamide, dimethylformamide-/acetone or glacial acetic acid, where appropriate with the addition of an acid such as hydrochloric acid at temperatures between 0 and 50° C., but preferably at room temperature, and under a pressure of from 1 to 7 bar, but preferably of from 1 to 5 bar, of hydrogen.

Where appropriate in the reactions described above it is possible for reactive groups which are present, such as hydroxy, carboxy, amino, alkylamino or imino groups, to be protected during the reaction by conventional protecting groups which are eliminated again after the reaction. For example, suitable as protecting group for a hydroxy group is the methoxy, benzyloxy, trimethylsilyl, acetyl, benzoyl, tert-butyl, trityl, benzyl or tetrahydropyranyl group, as protecting group for a carboxyl group is the trimethylsilyl, methyl, ethyl, tert-butyl, benzyl or tetrahydropyranyl group and as protecting group for an amino, alkylamino or imino group is the acetyl, trifluoroacetyl, benzoyl, ethoxycarbonyl, tert-butoxycarbonyl, benzyloxycarbonyl, benzyl, methoxybenzyl or 2,4-dimethoxybenzyl group and for the amino group additionally is the phthalyl group, as protecting group for an ethynyl group is the trimethylsilyl, diphenylmethylsilyl, tert-butyldimethylsilyl or 1-hydroxy-1-methylethyl group.

Further protecting groups and their elimination are described in T. W. Greene, P. G. M. Wuts, "Protective Groups in Organic Synthesis", Wiley, 1991 and 1999.

Where appropriate the subsequent elimination of a protecting group used takes place for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether cleavage, e.g. in the presence of iodotrimethylsilane, at temperatures between 0 and 100° C., preferably at temperatures between 10 and 50° C.

However, elimination of a benzyl, methoxybenzyl or benzyloxycarbonyl group takes place for example by hydrogenolysis, e.g. with hydrogen in the presence of a catalyst such as palladium/carbon in a solvent such as methanol, ethanol, ethyl acetate, dimethylformamide, dimethylformamide/acetone or glacial acetic acid, where appropriate with the addition of an acid such as hydrochloric acid at temperatures between 0 and 50° C., but preferably at room temperature, and under a pressure of from 1 to 7 bar, but preferably of from 1 to 5 bar, of hydrogen. Elimination of a methoxybenzyl group can also take place in the presence of an oxidizing agent such as cerium(IV) ammonium nitrate in a solvent such as methylene chloride, acetonitrile or acetonitrile/water at temperatures between 0 and 50° C., but preferably at room temperature. Elimination of a methoxy group preferably takes place in the presence of boron tribromide in a solvent such as methylene chloride at temperatures between −35 and −25° C.

However, elimination of a 2,4-dimethoxybenzyl group preferably takes place in trifluoroacetic acid in the presence of anisole.

Elimination of a tert-butyl or tert-butoxycarbonyl group preferably takes place by treatment with an acid such as trifluoroacetic acid or hydrochloric acid, where appropriate with use of a solvent such as methylene chloride, dioxane or ether.

Elimination of a phthalyl group preferably takes place in the presence of hydrazine or a primary amine such as methylamine, ethylamine or n-butylamine in a solvent such as methanol, ethanol, isopropanol, toluene/water or dioxane at temperatures between 20 and 50° C.

Elimination of an allyloxycarbonyl group takes place by treatment with a catalytic amount of tetrakis(triphenylphosphine)palladium(0), preferably in a solvent such as tetrahydrofuran and preferably in the presence of an excess of a base such as morpholine or 1,3-dimedone at temperatures between 0 and 100° C., preferably at room temperature and under inert gas, or by treatment with a catalytic amount of tris(triphenylphosphine)rhodium(I) chloride in a solvent such as aqueous ethanol and, optionally, in the presence of a base such as 1,4-diazabicyclo[2.2.2]octane at temperatures between 20 and 70° C.

The resulting compounds of the general formula I can furthermore be separated into their enantiomers and/or diastereomers.

Thus, for example, separation into their optical antipodes of the resulting compounds of the general formula I which occur in racemates is possible by methods known per se (see Allinger N. L. and Eliel E. L. in "Topics in Stereochemistry", Vol. 6, Wiley Interscience, 1971) and compounds of the general formula I having at least two asymmetric carbon atoms on the basis of their physicochemical differences by methods known per se, e.g. by chromatography and/or fractional crystallization, into their diastereomers which, if they result in racemic form, can subsequently be separated into the enantiomers as mentioned above.

Separation of enantiomers preferably takes place by separation on chiral phase columns or by recrystallization from an optically active solvent or by reaction with an optically active substance which forms salts or derivatives such as, for example, esters or amides with the racemic compound, especially acids and their activated derivatives or alcohols, and separation of the diastereomeric salt mixture or derivatives obtained in this way, e.g. on the basis of different solubilities, it being possible to liberate the free antipodes from pure diastereomeric salts or derivatives by the action of suitable agents. Optically active acids which are used in particular are, for example, the D and L forms of tartaric acid or dibenzoyltartaric acid, di-o-tolyltartaric acid, malic acid, mandelic acid, camphorsulphonic acid, glutamic acid, aspartic acid or quinic acid. A suitable optically active alcohol is, for example, (+)- or (−)-menthol and a suitable optically active acyl group in amides is, for example, the (+)- or (−)-menthyloxycarbonyl group.

The resulting compounds of the formula I can furthermore be converted into their salts, especially for pharmaceutical use into their physiologically acceptable salts with inorganic or organic acids. Examples of suitable acids are hydrochloric acid, hydrobromic acid, sulphuric acid, methanesulphonic acid, phosphoric acid, fumaric acid, succinic acid, lactic acid, citric acid, tartaric acid or maleic acid.

The novel compounds of the formula I obtained in this way may additionally, if they comprise a carboxy group, optionally subsequently be converted into their salts with inorganic or organic bases, in particular for pharmaceutical use into their physiologically acceptable salts. Examples of suitable bases in this connection are sodium hydroxide, potassium hydroxide, cyclohexylamine, ethanolamine, diethanolamine and triethanolamine.

As already hereinbefore mentioned, the compounds of the general formula I and their tautomers, their enantiomers, their diastereomers and their physiologically acceptable salts have valuable pharmacological properties, especially an antithrombotic effect, which is preferably based on an effect influencing thrombin or factor Xa, for example on a thrombin-inhibiting or factor Xa-inhibiting effect, on an effect prolonging the aPTT time and on an inhibitory effect on related serine proteases such as, for example, urokinase, factor VIIa, factor IX, factor XI and factor XII.

The compounds detailed in the experimental section were investigated for their effect on inhibition of factor Xa as follows:

Method:

Enzyme-kinetic measurement with chromogenic substrate. The amount of p-nitroaniline (pNA) liberated by human factor Xa from the colourless chromogenic substrate is determined by photometry at 405 nm. It is proportional to the activity of the enzyme employed. Inhibition of the enzymic activity by the test substance (relative to the solvent control) is measured at various test substance concentrations, and the $IC_{50}$ is calculated therefrom as the concentration which inhibits the factor Xa employed by 50%.

Material:

Tris(hydroxymethyl)aminomethane buffer (100 mmol) and sodium chloride (150 mmol), pH 8.0 plus 1 mg/ml human albumin fraction V, protease-free Faktor Xa (Calbiochem), spec. activity: 217 IU/mg, final concentration: 7 IU/ml per reaction mixture S 2765 substrate (Chromogenix), final concentration: 0.3 mM/l (1 KM) per reaction mixture Test substance: final concentration 100, 30, 10, 3, 1, 0.3, 0.1, 0.03, 0.01, 0.003, 0.001 µmol/l Procedure: 10 µl of a 23.5-fold concentrated starting solution of the test substance or solvent (control), 175 µl of TRIS/HSA buffer and 25 µl of factor Xa working solution of 65.8 U/l are incubated at 37° C. for 10 minutes. After addition of 25 µl of S 2765 working solution (2.82 mmol/l), the sample is measured in a photometer (SpectraMax 250) at 405 nm and at 37° C. for 600 seconds.

Evaluation:

1. Determination of the maximum increase (deltaOD/minutes) over 21 measurement points.
2. Determination of the % inhibition relative to the solvent control.
3. Construction of a dose-effect plot (% inhibition vs substance concentration).
4. Determination of the $IC_{50}$ by interpolation of the X value (substance concentration) of the dose-effect plot at Y=50% inhibition.

All the tested compounds showed $IC_{50}$ values below 100 µmol/l.

The compounds prepared according to the invention are generally well acceptable.

Owing to their pharmacological properties, the novel compounds and their physiologically acceptable salts are suitable for the prevention and treatment of venous and arterial thrombotic disorders, such as, for example, prevention and treatment of deep leg vein thromboses, prevention of reocclusions after bypass operations or angioplasty (PT(C)A) and of occlusion associated with peripheral arterial disorders, and prevention and treatment of pulmonary embolism, of disseminated intravascular coagulation and of severe sepsis, prevention and prophylaxis of DVT in patients with exacerbation of COPD, treatment of ulcerative colitis, prophylaxis and treatment of coronary thrombosis, prophylaxis of stroke and prevention of occlusion of shunts. In addition, the compounds according to the invention are suitable for antithrombotic support in a thrombolytic treatment such as, for example, with alteplase, reteplase, tenecteplase, staphylokinase or streptokinase, for preventing long-term restinosis after PT(C)A, for the prophylaxis and treatment of ischaemic events in patients with all types of coronary heart disease, for preventing metastasis and the growth of tumours and of inflammatory processes, e.g. in the treatment of pulmonary fibrosis, for the prophylaxis and treatment of rheumatoid arthritis, for the prophylaxis or prevention of fibrin-dependent tissue adhesions and/or formation of scar tissue, and for promoting wound-healing processes. The novel compounds and their physiologically acceptable salts can be employed therapeutically in combination with acetylsalicylic acid, with inhibitors of platelet aggregation such as fibrinogen receptor antagonists (e.g. abciximab, eptifibatide, tirofiban, roxifiban), with physiological activators and inhibitors of the coagulation system and their recombinant analogues (e.g. protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

The dosage required to achieve a corresponding effect is conveniently from 0.01 to 3 mg/kg, preferably 0.03 to 1.0 mg/kg, on intravenous administration and from 0.03 to 30 mg/kg, preferably 0.1 to 10 mg/kg, on oral administration, in each case 1 to 4× daily.

For this purpose, the compounds of the formula I prepared according to the invention can be incorporated, where appropriate in combination with other active substances, together with one or more inert conventional carriers and/or diluents, e.g. with maize starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional pharmaceutical preparations such as tablets, coated tablets, capsules, powders, suspensions or suppositories.

The following examples are intended to explain the invention in detail without, however, restricting the scope thereof:

Experimental Section

In general, melting points, IR, UV, $^1$H-NMR and/or mass spectra are available for the prepared compounds. Unless indicated otherwise, $R_f$ values were determined using precoated silica gel 60 $F_{254}$ TLC plates (E. Merck, Darmstadt, article No. 1.05714) without tank saturation. The $R_f$ values determined with the designation alox were determined using precoated alumina 60 $F_{254}$ TLC plates (E. Merck, Darmstadt, article No. 1.05713) without tank saturation. The $R_f$ values determined with the designation reversed phase 8 were determined using precoated RP-8 $F_{254}$S TLC plates (E. Merck, Darmstadt, article No. 1.15684) without tank saturation. The ratios indicated for the mobile phases relate to volumetric units of the respective solvents. Silica gel supplied by Millipore (MATREX™, 35-70 μm) was used for chromatographic purifications. In the absence of details about the configuration, it is unknown whether the products are pure stereoisomers or enantiomer/diastereomer mixtures.

The following abbreviations are used in the descriptions of the experiments:

| | |
|---|---|
| Boc | tert-butoxycarbonyl |
| DIPEA | N-ethyldiisopropylamine |
| DMSO | dimethyl sulphoxide |
| DMF | N,N-dimethylformamide |
| Pd(dppf)Cl$_2$ | palladium(II) [1,1'-bis(diphenylphosphino)ferrocene] chloride |
| sat. | saturated |
| in vac. | in vacuo |
| conc. | concentrated |
| NMM | N-methylmorpholine |
| NMP | N-methylpyrrolidin-2-one |
| quant. | quantitative |
| $R_f$ | retention factor |
| $R_t$ | retention time |
| rac. | racemic |
| TBTU | O-(benzotriazol-1-yl)-N,N,N',N'-tetramethyluronium tetrafluoroborate |
| TEA | triethylamine |
| TFA | trifluoroacetic acid |
| THF | tetrahydrofuran |
| tert. | tertiary |

EXAMPLE 1

Beispiel 1

5-Ethynyl-N-{1-methyl-1-[3-methyl-4-(3-oxomorpholin-4-yl)phenyl-carbamoyl]ethyl}thiophene-2-carboxamide

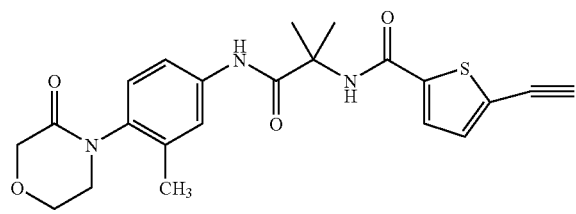

(a) 2-N-Boc-Amino-N'-[3-methyl-4-(3-oxomorpholin-4-yl)phenyl]isobutyramide 1.10 ml (10.0 mmol) of NMM and 2.57 g (8.00 mmol) of TBTU are added to a stirred solution of 1.52 g (7.50 mmol) of 2-N-Boc-aminoisobutyric acid in 5.0 ml of DMF and, after stirring for 5 min, 1.55 g (7.5 mmol) of 3-methyl-4-(3-oxomorpholin-4-yl)aniline are added. After 5 h, a further 0.13 g of 2-N-Boc-aminoisobutyric acid is added, and the mixture is stirred at 30° C. for a further 15 min and poured into ice-water. Sodium bicarbonate solution is added, and the mixture is extracted with ethyl acetate. The combined organic phases are washed successively with sat. bicarbonate solution, with 0.25 M KHSO$_4$ solution and sat. NaCl solution and dried with MgSO$_4$. After concentration in vac., slightly impure title compound is obtained.

Crude yield: 92% $R_f$: 0.67 (silica gel; ethyl acetate/ethanol=9:1) C$_{20}$H$_{29}$N$_3$O$_5$ (391.46) Mass spectrum: (M+H)$^+$= 392

(b) 2-Amino-N-[3-methyl-4-(3-oxomorpholin-4-yl)phenyl]isobutyramide

A suspension of 8.95 g (22.9 mmol) of 2-N-Boc-amino-N'-[3-methyl-4-(3-oxomorpholin-4-yl)phenyl]isobutyramide is stirred with 135 ml of 6 molar hydrochloric acid in 30 ml of dioxane for 1 h. The reaction mixture is washed with diethyl ether, poured into ice/ammonia solution and extracted 6× with 100 ml of methylene chloride each time. The combined organic phases are washed with water, dried with MgSO$_4$ and concentrated in vac.

Crude yield: 83% $R_f$: 0.65 (silica gel; ethyl acetate/ethanol=9:1+1% conc. ammonia solution) C$_{15}$H$_{21}$N$_3$O$_3$ (291.35) Mass spectrum: (M+H)$^+$=292

(c) 5-Bromo-N-{1-methyl-1-[3-methyl-4-oxomorpholin-4-yl)phenylcarbamoyl]ethyl}thiophene-2-carboxamide 0.770 ml (7.00 mmol) of NMM and 1.06 g (3.3 mmol) of TBTU are added to a stirred solution of 0.642 g (3.10 mmol) of 5-bromothiophene-2-carboxylic acid in 2.0 ml of DMF and, after stirring for 5 min, 0.900 g (3.10 mmol) of 2-amino-N-[3-methyl-4-(3-oxomorpholin-4-yl)phenyl]isobutyramide are added. After 4 h, the mixture is poured into ice-water, mixed with sodium bicarbonate solution and extracted with ethyl acetate. The combined organic phases are washed successively with sat. bicarbonate solution, with 0.25 M KHSO$_4$ solution and sat. NaCl solution and dried with MgSO$_4$. Concentration in vac. is followed by addition of diethyl ether, filtration of the crystals with suction, washing with diethyl ether and drying at 60° C.

Yield: 91% $R_f$: 0.50 (silica gel; ethyl acetate/ethanol=9:1+ 1% conc. ammonia solution) C$_{20}$H$_{22}$BrN$_3$O$_4$S (480.38) Mass spectrum: (M+H)$^+$=480/482 (bromine isotopes)

(d) 5-(2-Trimethylsilylethynyl)-N-{1-methyl-1-[3-methyl-4-(3-oxomorpholin-4-yl)phenylcarbamoyl]ethyl}thiophene-2-carboxamide A solution of 1.00 g (2.08 mmol) of 5-bromo-N-{1-methyl-1-[3-methyl-4-(3-oxomorpholin-4-yl)phenylcarbamoyl]ethyl}thiophene-2-carboxamide, 40 mg (0.208 mmol) of copper(I) iodide, 0.62 g (4.16 mmol) of sodium iodide and 0.044 ml (0.416 mmol) of N,N-dimethylethylene-1,2-diamine in 2.5 ml of dioxane is stirred at 100° C. for 20 h, cooled to room temperature, diluted with conc. ammonia and water and extracted with ethyl acetate. The combined organic phases are extracted with ethyl acetate, dried with sodium sulphate and concentrated in vac. The crude product (0.86 g) is directly reacted further. A suspension of the above crude product (0.86 g), 0.45 ml (3.26 mmol) of trimethylsilylacetylene and 0.68 ml (4.8 mmol) of triethylamine in 10 ml of acetonitrile/20 ml of THF is saturated with argon several times, and 67 mg (0.082 mmol) of PdCl$_2$(dppf) and 15 mg (0.082 mmol) of copper(I) iodide are added. The initially reddish brown suspension becomes lemon-yellow after about 15 min. After stirring for 16 h, the mixture is diluted with ethyl acetate, washed with 5% ammonia solution, dried with sodium sulphate and concentrated in vac.

Yield: 78% (2 stages) R$_f$: 0.75 (silica gel; methylene chloride/ethanol=9:1) C$_{25}$H$_{31}$N$_3$O$_4$SSi (497.68) Mass spectrum: (M+H)$^+$=498 e) 5-Ethynyl-N-{1-methyl-1-[3-methyl-4-(3-oxomorpholin-4-yl)phenylcarbamoyl]ethyl}thiophene-2-carboxamide A mixture of 0.81 g (1.63 mmol) of 5-(2-trimethylsilylethynyl)-N-{1-methyl-1-[3-methyl-4-(3-oxomorpholin-4-yl)phenylcarbamoyl]ethyl}thiophene-2-carboxamide and 0.57 g (1.79 mmol) of tetrabutylammonium fluoride trihydrate in 30 ml of methylene chloride is stirred for 2 h and then the organic phase is washed 3× with water, dried with sodium sulphate, filtered and concentrated in vac. The crude product is purified by chromatography (silica gel, methylene chloride→methylene chloride:ethanol 25:1).

Yield: 85% R$_f$: 0.52 (silica gel; methylene chloride/ethanol=9:1) C$_{22}$H$_{23}$N$_3$O$_4$S (425.502) Mass spectrum: (M+H)$^+$=426(M−H)$^−$=424

EXAMPLE 2

5-Ethynyl-N-{3-[3-methyl-4-(3-oxomorpholin-4-yl)phenylcarbamoyl]-tetrahydrofuran-3-yl}thiophene-2-carboxamide

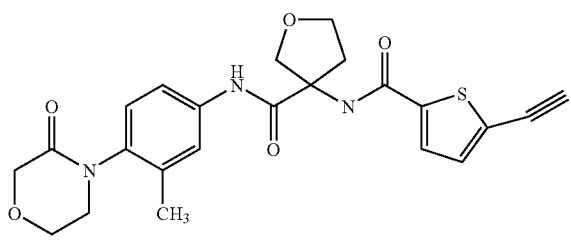

(a) 3-Boc-Amino-N-[3-chloro-4-(3-oxomorpholin-4-yl)phenyl]tetrahydrofuran-3-carboxamide Prepared analogously to Example 1a from 3-Boc-aminotetrahydrofuran-3-carboxylic acid and 3-methyl-4-(3-oxomorpholin-4-yl)aniline with TBTU and NMM in DMF.

Yield: 60% R$_f$: 0.53 (silica gel; methylene chloride/ethanol=9:1+ammonia) C$_{21}$H$_{29}$N$_3$O$_6$ (419.47) Mass spectrum: (M−H)$^−$=418

(b) 3-Amino-N-[3-methyl-4-(3-oxomorpholin-4-yl)phenyl]tetrahydrofuran-3-carboxamide 760 mg (1.81 mmol) of 3-Boc-amino-N-[3-methyl-4-(3-oxomorpholin-4-yl)phenyl]tetrahydrofuran-3-carboxamide are dissolved in ethanolic hydrochloric acid at room temperature and stirred at room temperature for 4 hours. After concentration in vac., the title compound is obtained as HCl salt.

Yield: 720 mg (quantitative) R$_f$: 0.76 (RP-8 silica gel; MeOH:5% NaCl solution 6:4) C$_{16}$H$_{21}$N$_3$O$_4$*2HCl (392.28/319.36) Mass spectrum: (M+H)$^+$=320

(c) 5-Ethynylthiophene-2-carboxylic acid

A solution of 9.93 g (39 mmol) of ethyl-5-(2-trimethylsilyl)ethynyl-thiophenecarboxylic acid (see WO1996/03407 for preparation) in 50 ml of ethanol is stirred with 200 ml of 2M NaOH at 50° C. for 4 h. The mixture is then concentrated in vac., mixed with water and extracted 2× with methylene chloride. The aqueous phase is acidified with HCl and cooled, and the precipitate which separates out is filtered off with suction.

Yield: 4.8 g (80%) R$_f$: 0.24 (silica gel; methylene chloride: MeOH 95:5) C$_7$H$_4$O$_2$S*2HCl (152.17) Mass spectrum: (M−H)$^−$=151

(d) 5-Ethynyl-N-{3-[3-methyl-4-(3-oxomorpholin-4-yl)phenylcarbamoyl]-tetrahydrofuran-3-yl}thiophene-2-carboxamide Prepared analogously to Example 1a from 5-ethynylthiophene-2-carboxylic acid and 3-amino-N-[3-methyl-4-(3-oxomorpholin-4-yl)phenyl]tetrahydro-furan-3-carboxamide with TBTU and NMM in DMF.

Yield: 74% R$_f$: 0.44 (silica gel; methylene chloride/ethanol=9:1) C$_{23}$H$_{23}$N$_3$O$_5$S (453.512) Mass spectrum: (M+H)$^+$=454(M−H)$^−$=452

The two enantiomers can be separated by a chiral column of Chiralpak OD 250 mm×4.6 mm with a 70% hexane/30% ethanol+0.1% diethylamine mixture at a flow rate of 1 ml/min at 40° C. (Rt=12.8 min and Rt=20.1 min).

EXAMPLE 3

(R)-5-Ethynyl-N-{2-methoxy-1-[3-methyl-4-(3-oxomorpholin-4-yl)phenylcarbamoyl]ethyl}thiophene-2-carboxamide

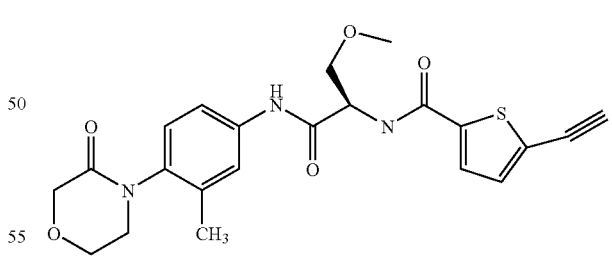

Prepared analogously to Example 1a from 5-ethynylthiophene-2-carboxylic acid and 2-(R)-amino-3-methoxy-N-[3-methyl-4-(3-oxomorpholin-4-yl)phenyl]propionamide with TBTU and NMM in DMF.

Yield: 62% R$_f$: 0.54 (silica gel; ethyl acetate/ethanol=9:1+1 drop of ammonia) C$_{22}$H$_{23}$N$_3$O$_5$S (441.501) Mass spectrum: (M+H)$^+$=442(M−H)$^−$=440

The following compounds were prepared analogously:

| No. | Structural formula Name | Mass peak(s) | $R_f$ |
|---|---|---|---|
| 4 | 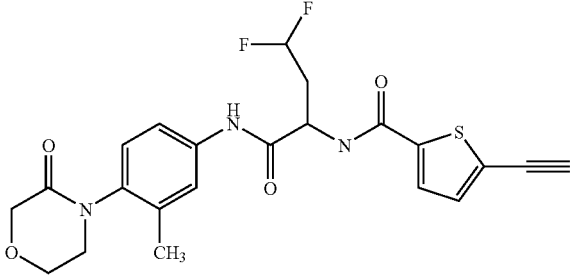<br>5-Ethynyl-N-{3,3-difluoro-1-[3-methyl-4-(3-oxomorpholin-4-yl)phenylcarbamoyl]propyl}thiophene-2-carboxamide | $(M + H)^+ = 462$ | 0.60 (silica gel, $CH_2Cl_2/C_2H_5OH$ 9:1) |
| 5 | 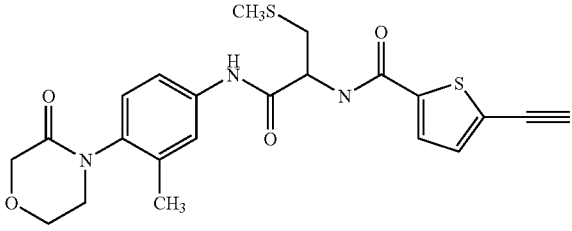<br>5-Ethynyl-N-{2-methylsulphanyl-1-[3-methyl-4-(3-oxomorpholin-4-yl)phenylcarbamoyl]ethyl}thiophene-2-carboxamide | $(M - H)^- = 456$ | 0.58 (silica gel, $CH_2Cl_2/C_2H_5OH$ 9:1) |
| 6 | 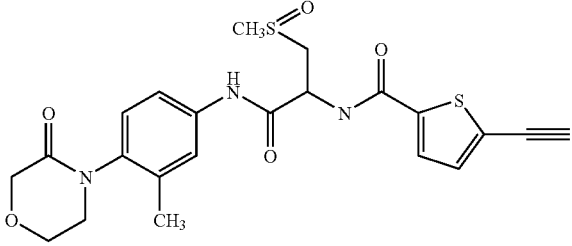<br>5-Ethynyl-N-{2-methylsulphinyl-1-[3-methyl-4-(3-oxomorpholin-4-yl)phenylcarbamoyl]ethyl}thiophene-2-carboxamide | $(M + H)^+ = 474$ | 0.44 (silica gel, $CH_2Cl_2/C_2H_5OH$ 9:1) |
| 7 | 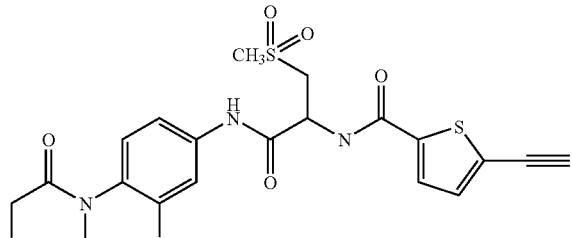<br>5-Ethynyl-N-{2-methylsulphonyl-1-[3-methyl-4-(3-oxomorpholin-4-yl)phenylcarbamoyl]ethyl}thiophene-2-carboxamide | $(M + H)^+ = 490$<br>$(M - H)^- = 488$ | 0.45 (silica gel, $CH_2Cl_2/C_2H_5OH$ 9:1) |

-continued

| No. | Structural formula Name | Mass peak(s) | $R_f$ |
|---|---|---|---|
| 8 | 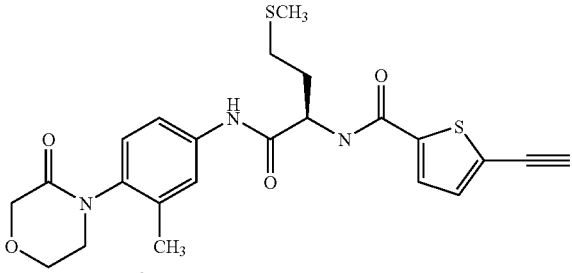<br>(R)-5-Ethynyl-N-{3-methylsulphanyl-1-[3-methyl-4-(3-oxomorpholin-4-yl)phenylcarbamoyl]propyl}thiophene-2-carboxamide | $(M + H)^+ = 472$ | 0.25 (silica gel, ethyl acetate/petroleum ether 9:1) |
| 9 | 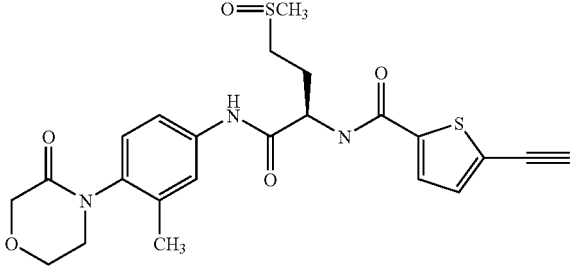<br>(R)-5-Ethynyl-N-{3-methylsulphinyl-1-[3-methyl-4-(3-oxomorpholin-4-yl)phenylcarbamoyl]propyl}thiophene-2-carboxamide | $(M + H)^+ = 488$ | 0.3 (silica gel, $CH_2Cl_2/C_2H_5OH$ 9:1) |
| 10 | 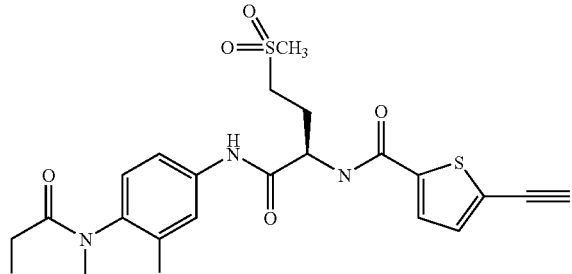<br>(R)-5-Ethynyl-N-{3-methylsulphonyl-1-[3-methyl-4-(3-oxomorpholin-4-yl)phenylcarbamoyl]propyl}thiophene-2-carboxamide | $(M - H)^- = 502$ | 0.4 (silica gel, $CH_2Cl_2/C_2H_5OH$ 9:1) |
| 11 | 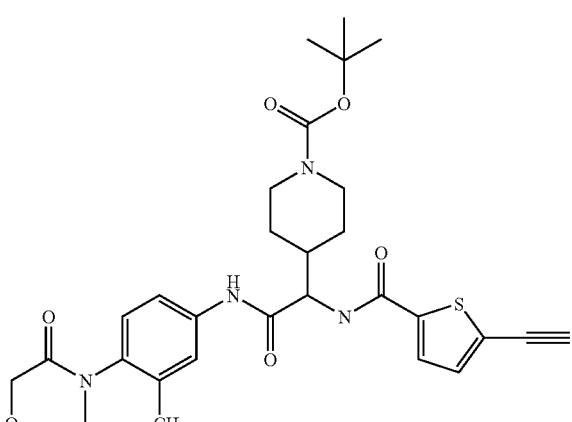<br>5-Ethynyl-N-{C-[3-methyl-4-(3-oxomorpholin-4-yl)phenylcarbamoyl]-C-(1-tert-butoxycarbonyl)piperidin-4-ylmethyl}thiophene-2-carboxamide | $(M - H)^- = 579$ | 0.5 (silica gel, $CH_2Cl_2/C_2H_5OH$ 9:1) |

-continued

| No. | Structural formula Name | Mass peak(s) | $R_f$ |
|---|---|---|---|
| 12 | 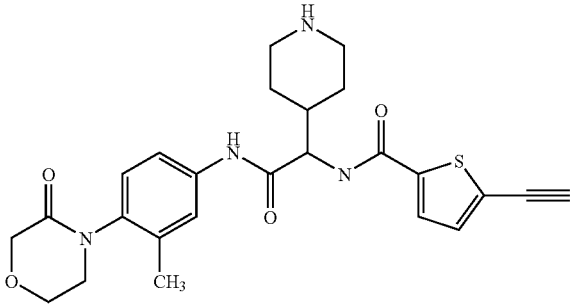<br>5-Ethynyl-N-{C-[3-methyl-4-(3-oxomorpholin-4-yl)phenylcarbamoyl]-C-piperidin-4-ylmethyl)thiophene-2-carboxamide | $(M + H)^+ = 481$ | 0.2 (silica gel, $CH_2Cl_2/C_2H_5OH$ 9:1) |
| 13 | 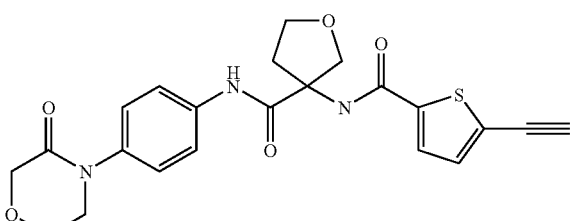<br>5-Ethynyl-N-{3-[4-(3-oxomorpholin-4-yl)phenylcarbamoyl]tetrahydrofuran-3-yl}thiophene-2-carboxamide | $(M - H)^- = 438$ | 0.4 (silica gel, $CH_2Cl_2/C_2H_5OH$ 9:1) |
| 14 | 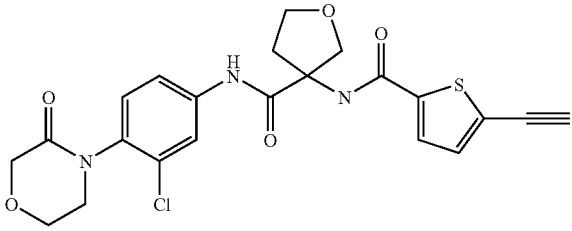<br>5-Ethynyl-N-{3-[3-chloro-4-(3-oxomorpholin-4-yl)phenylcarbamoyl]-tetrahydrofuran-3-yl}thiophene-2-carboxamide | $(M - H)^- = 472/474$ | 0.48 (silica gel, $CH_2Cl_2/C_2H_5OH$ 9:1) |
| 15 | 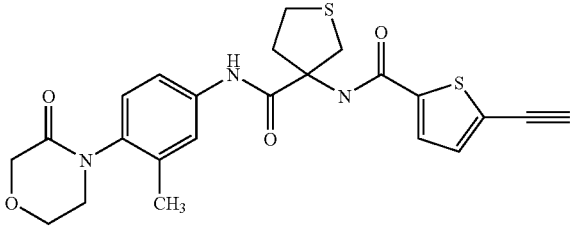<br>5-Ethynyl-N-{3-[3-methyl-4-(3-oxomorpholin-4-yl)phenylcarbamoyl]-tetrahydrothiophen-3-yl}thiophene-2-carboxamide | $(M - H)^- = 468$ | 0.60 (silica gel, $CH_2Cl_2/C_2H_5OH$ 9:1) |
| 16 | 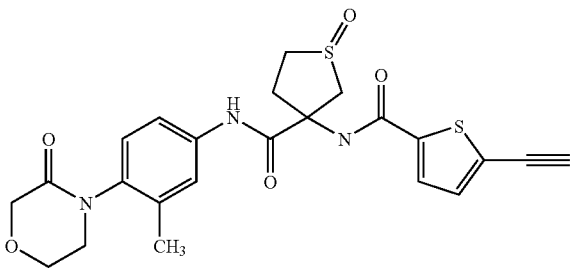<br>5-Ethynyl-N-{3-[3-methyl-4-(3-oxomorpholin-4-yl)phenylcarbamoyl]-1-oxotetrahydrothiophen-3-yl}thiophene-2-carboxamide | $(M + H)^+ = 486$ | 0.34 (silica gel, $CH_2Cl_2/C_2H_5OH$ 9:1) |

-continued

| No. | Structural formula Name | Mass peak(s) | $R_f$ |
|---|---|---|---|
| 17 | 5-Ethynyl-N-{3-[3-methyl-4-(3-oxomorpholin-4-yl)phenylcarbamoyl]-1-dioxotetrahydrothiophen-3-yl}thiophene-2-carboxamide | $(M + H)^+ = 502$ | 0.50 (silica gel, $CH_2Cl_2/C_2H_5OH$ 9:1) |
| 18 | 5-Ethynyl-N-{3-[4-(2-oxopyrrolidin-1-yl)phenylcarbamoyl]tetrahydrofuran-3-yl}thiophene-2-carboxamide | $(M + H)^+ = 424$ | 0.61 (silica gel, $CH_2Cl_2/C_2H_5OH$ 9:1) |
| 19 | 5-Ethynyl-N-{3-[4-(3-methyl-2-oxoimidazolidin-1-yl)phenylcarbamoyl]tetrahydrofuran-3-yl}thiophene-2-carboxamide | $(M + H)^+ = 439$ | 0.53 (silica gel, $CH_2Cl_2/C_2H_5OH$ 9:1) |

5-ethynyl-N-{1-methyl-1-[3-trifluoromethyl-4-(3-oxomorpholin-4-yl)phenylcarbamoyl]ethyl}thiophene-2-carboxamide 5-ethynyl-N-{1-methyl-1-[3-bromo-4-(3-oxomorpholin-4-yl)phenylcarbamoyl]ethyl}thiophene-2-carboxamide 5-ethynyl-N-{1-[3-methyl-4-(3-oxomorpholin-4-yl)phenylcarbamoyl]ethyl}thiophene-2-carboxamide 5-ethynyl-N-{1-[3-methyl-4-(3-oxomorpholin-4-yl)phenylcarbamoyl]-butyl}thiophene-2-carboxamide 5-ethynyl-N-{2-methoxy-1-[3-methyl-4-(3-oxomorpholin-4-yl)phenylcarbamoyl]propyl}thiophene-2-carboxamide 5-ethynyl-N-{2-dimethoxyphosphoryl-1-[3-methyl-4-(3-oxomorpholin-4-yl)phenylcarbamoyl]ethyl}thiophene-2-carboxamide 5-ethynyl-N-{3-methoxycarbonyl-1-[3-methyl-4-(3-oxomorpholin-4-yl)phenylcarbamoyl]propyl}thiophene-2-carboxamide 5-ethynyl-N-{3-hydroxycarbonyl-1-[3-methyl-4-(3-oxomorpholin-4-yl)phenylcarbamoyl]propyl}thiophene-2-carboxamide 5-ethynyl-N-{3-(tetrazol-5-yl)-1-[3-methyl-4-(3-oxomorpholin-4-yl)phenylcarbamoyl]propyl}thiophene-2-carboxamide 5-ethynyl-N-{2-phenyl-1-[3-methyl-4-(3-oxomorpholin-4-yl)phenylcarbamoyl]ethyl}thiophene-2-carboxamide 5-ethynyl-N-{2-(pyridin-3-yl)-1-[3-methyl-4-(3-oxomorpholin-4-yl)phenylcarbamoyl]ethyl}thiophene-2-carboxamide 5-ethynyl-N-{1-(pyridin-3-yl)-1-[3-methyl-4-(3-oxomorpholin-4-yl)phenylcarbamoyl]methyl}thiophene-2-carboxamide 5-ethynyl-N-{1-(1H-imidazol-4-yl)-1-[3-methyl-4-(3-oxomorpholin-4-yl)phenylcarbamoyl]methyl}thiophene-2-carboxamide 5-ethynyl-N-{1-(1H-1-methylimidazol-4-yl)-1-[3-methyl-4-(3-oxomorpholin-4-yl)phenylcarbamoyl]methyl}thiophene-2-carboxamide 5-ethynyl-N-{1-(1H-1-methylpyrazol-3-yl)-1-[3-methyl-4-(3-oxomorpholin-4-yl)phenylcarbamoyl]methyl}thiophene-2-carboxamide 5-ethynyl-N-{1-(furan-2-yl)-1-[3-methyl-4-(3-oxomorpholin-4-yl)phenylcarbamoyl]methyl}thiophene-2-carboxamide 5-ethynyl-N-{1-methoxymethyl-1-[3-methyl-4-(3-oxomorpholin-4-yl)phenylcarbamoyl]ethyl}thiophene-2-carboxamide 5-ethynyl-N-{1-methylsulphanylmethyl-1-[3-methyl-4-(3-oxomorpholin-4-yl)phenylcarbamoyl]ethyl}thiophene-2-carboxamide 5-ethynyl-N-{1-trifluoromethyl-1-[3-methyl-4-(3-oxomorpholin-4-yl)phenylcarbamoyl]ethyl}thiophene-2-carboxamide 5-ethynyl-N-{1-methyl-1-[6-fluoro-3-methyl-4-(3-oxomorpholin-4-yl)phenylcarbamoyl]ethyl}thiophene-2-carboxamide 5-ethynyl-N-{1-[3-methyl-4-(3-oxomorpholin-4-yl)phenylcarbamoyl]cyclobut-1-yl}thiophene-2-carboxamide 5-ethynyl-N-{1-[3-methyl-4-(3-oxomorpholin-4-yl)phenylcarbamoyl]cyclopent-1-yl}thiophene-2-carboxamide 5-ethynyl-N-{1-[3-methyl-4-(3-oxomorpholin-4-yl)phenylcarbamoyl]cyclohex-1-yl}thiophene-2-carboxamide 5-ethynyl-N-{3-[4-(3-oxomorpholin-4-yl)phenylcarbamoyl]tetrahydrofuran-3-yl}thiophene-2-carboxamide 5-ethynyl-N-{3-[3-bromo-4-(3-oxomorpholin-4-yl)phenylcarbamoyl]tetrahydrofuran-3-yl}thiophene-2-carboxamide 5-ethynyl-N-{3-[3-methyl-4-(3-oxomorpholin-4-yl)phenylcarbamoyl]oxetan-3-yl}thiophene-2-carboxamide 5-ethynyl-N-{3-[3-methyl-4-(3-oxomorpholin-4-yl)phenylcarbamoyl]thietan-3-yl}thiophene-2-carboxamide 5-ethynyl-N-{3-[3-methyl-4-(3-oxomorpholin-4-yl)phenylcarbamoyl]-1,1-dioxothietan-3-yl}thiophene-2-carboxamide 5-ethynyl-N-{5-[3-methyl-4-(3-oxomorpholin-4-yl)phenylcarbamoyl]-2-oxo-1,3-dioxinane-5-yl}thiophene-2-carboxamide 5-ethynyl-N-{5-[3-methyl-4-(3-oxomorpholin-4-yl)phenylcarbamoyl]-2-oxohexahydropyrimidin-5-yl}thiophene-2-carboxamide 5-ethynyl-N-{3-[3-methyl-4-(3-oxomorpholin-4-yl)phenylcarbamoyl]-5-oxopyrrolidin-3-yl}thiophene-2-carboxamide 5-ethynyl-N-{1-methyl-3-[3-methyl-4-(3-oxomorpholin-4-yl)phenylcarbamoyl]-5-oxo-pyrrolidin-3-yl}thiophene-2-carboxamide 5-ethynyl-N-{3-[3-methyl-4-(3-oxomorpholin-4-yl)phenylcarbamoyl]pyrrolidin-3-yl}thiophene-2-carboxamide 5-ethynyl-N-{1-methyl-3-[3-methyl-4-(3-oxomorpholin-4-yl)phenylcarbamoyl]pyrrolidin-3-yl}thiophene-2-carboxamide 5-ethynyl-N-{1-acetyl-3-[3-methyl-4-(3-oxomorpholin-4-yl)phenylcarbamoyl]pyrrolidin-3-yl}thiophene-2-carboxamide 5-ethynyl-N-{3-[3-methyl-4-(3-oxomorpholin-4-yl)phenylcarbamoyl]acetidin-3-yl}thiophene-2-carboxamide 5-ethynyl-N-{3-[5-(3-oxomorpholin-4-yl)pyridyl-2-carbamoyl]tetrahydrofuran-3-yl}thiophene-2-carboxamide 5-ethynyl-N-{3-[3-methyl-4-(2-oxopyrrolidin-1-yl)phenylcarbamoyl]tetrahydrofuran-3-yl}thiophene-2-carboxamide 5-ethynyl-N-{3-[3-methyl-4-(2-oxo-5-methylpyrrolidin-1-yl)phenylcarbamoyl]tetrahydrofuran-3-yl}thiophene-2-carboxamide 5-ethynyl-N-{3-[3-methyl-4-(2-oxo-4-methyloxazolidin-3-yl)phenylcarbamoyl]tetrahydrofuran-3-yl}thiophene-2-carboxamide 5-ethynyl-N-{3-[3-methyl-4-(2-oxo-4,4-dimethyloxazolidin-3-yl)phenylcarbamoyl]tetrahydrofuran-3-yl}thiophene-2-carboxamide 5-ethynyl-N-{3-[3-methyl-4-(2-oxo-5,5-dimethylpyrrolidin-1-yl)phenylcarbamoyl]tetrahydrofuran-3-yl}thiophene-2-carboxamide 5-ethynyl-N-{3-[3-methyl-4-(2-oxooxazolidin-3-yl)phenylcarbamoyl]tetrahydrofuran-3-yl}thiophene-2-carboxamide 5-ethynyl-N-{3-[3-methyl-4-(2-oxoimidazolidin-1-yl)phenylcarbamoyl]tetrahydrofuran-3-yl}thiophene-2-carboxamide 5-ethynyl-N-{3-[3-methyl-4-(3-methyl-2-oxoimidazolidin-1-yl)phenylcarbamoyl]tetrahydrofuran-3-yl}thiophene-2-carboxamide 5-ethynyl-N-{1-methyl-1-[3-methyl-4-(2-oxopiperidin-1-yl)phenylcarbamoyl]ethyl}thiophene-2-carboxamide 5-ethynyl-N-{1-methyl-1-[3-methyl-4-(2-oxoperhydro-1,3-oxazin-3-yl)phenylcarbamoyl]ethyl}thiophene-2-carboxamide 5-ethynyl-N-{1-methyl-1-[3-methyl-4-(2-oxotetrahydropyrimidin-1-yl)phenylcarbamoyl]ethyl}thiophene-2-carboxamide 5-ethynyl-N-{1-methyl-1-[3-methyl-4-(2-oxopiperazin-1-yl)phenylcarbamoyl]ethyl}thiophene-2-carboxamide 5-ethynyl-N-{1-methyl-1-[3-methyl-4-(2-oxo-4-methylpiperazin-1-yl)phenylcarbamoyl]ethyl}thiophene-2-carboxamide 5-ethynyl-N-{1-methyl-1-[3-methyl-4-(1,1-dioxoperhydro-1,2-thiazin-2-yl)phenylcarbamoyl]ethyl}thiophene-2-carboxamide 5-ethynyl-N-{1-methyl-1-[3-methyl-4-(2-iminopiperidin-1-yl)phenylcarbamoyl]ethyl}thiophene-2-carboxamide 5-ethynyl-N-{1-methyl-1-[3-methyl-4-(3-iminomorpholin-4-yl)phenylcarbamoyl]ethyl}thiophene-2-carboxamide 5-ethynyl-N-{1-methyl-1-[3-methyl-4-(2-iminoperhydroazepin-1-yl)phenylcarbamoyl]ethyl}thiophene-2-carboxamide 5-ethynyl-N-{1-methyl-1-[3-methyl-4-(5-oxoperhydro-1,4-oxazepin-4-yl)phenylcarbamoyl]ethyl}thiophene-2-carboxamide 5-ethynyl-N-{1-methyl-1-[3-methyl-4-(2-oxoperhydro-1,3-oxazepin-3-yl)phenylcarbamoyl]ethyl}thiophene-2-carboxamide 5-ethynyl-N-{1-[3-chloro-4-(5-cyaniminoperhydro-1,4-oxazepin-4-yl)phenylcarbamoyl]ethyl}thiophene-2-carboxamide 5-ethynyl-N-{1-[3-methyl-4-(5-hydroxyiminoperhydro-1,4-oxazepin-4-yl)phenylcarbamoyl]ethyl}thiophene-2-carboxamide The following examples describe the production of pharmaceutical preparations which comprise any compound of the general formula I as active ingredient:

EXAMPLE A

Dry Ampoule with 75 mg of Active Ingredient per 10 ml

Composition:

| Active ingredient | 75.0 mg |
|---|---|
| Mannitol | 50.0 mg |
| Water for injections | ad 10.0 ml |

Preparation:

Active ingredient and mannitol are dissolved in water. The charged ampoules are freeze dried. Water for injections is used to dissolve to give the solution ready for use.

EXAMPLE B

Dry Ampoule with 35 mg of Active Ingredient per 2 ml

Composition:

| Active ingredient | 35.0 mg |
|---|---|
| Mannitol | 100.0 mg |
| Water for injections | ad 2.0 ml |

Preparation:

Active ingredient and mannitol are dissolved in water. The charged ampoules are freeze dried. Water for injections is used to dissolve to give the solution ready for use.

EXAMPLE C

Tablet with 50 mg of Active Ingredient

Composition:

| (1) Active ingredient | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed and granulated with an aqueous solution of (4). (5) is admixed to the dry granules. Tablets are compressed from this mixture, biplanar with bevel on both sides and dividing groove on one side. Diameter of the tablets: 9 mm.

EXAMPLE D

Tablet with 350 mg of Active Ingredient

Composition:

| | | |
|---|---|---|
| (1) Active ingredient | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed and granulated with an aqueous solution of (4). (5) is admixed to the dry granules. Tablets are compressed from this mixture, biplanar with bevel on both sides and dividing groove on one side. Diameter of the tablets: 12 mm.

EXAMPLE E

Capsules with 50 mg of Active Ingredient

Composition:

| | |
|---|---|
| (1) Active ingredient | 50.0 mg |
| (2) Maize starch dried | 58.0 mg |
| (3) Lactose powdered | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into hard gelatin two-piece capsules of size 3 in a capsule-filling machine.

EXAMPLE F

Capsules with 350 mg of Active Ingredient

Composition:

| | |
|---|---|
| (1) Active ingredient | 350.0 mg |
| (2) Maize starch dried | 46.0 mg |
| (3) Lactose powdered | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into hard gelatin two-piece capsules of size 0 in a capsule-filling machine.

EXAMPLE G

Suppositories with 100 mg of Active Ingredient

1 Suppository Comprises:

| | |
|---|---|
| Active ingredient | 100.0 mg |
| Polyethylene glycol (M.W. 1500) | 600.0 mg |
| Polyethylene glycol (M.W. 6000) | 460.0 mg |
| Polyethylene sorbitan monostearate | 840.0 mg |
| | 2000.0 mg |

Preparation:

The polyethylene glycol is melted together with polyethylene sorbitan monostearate. At 40° C., the ground active substance is homogeneously dispersed in the melt. It is cooled to 38° C. and cast in slightly precooled suppository moulds.

What is claimed is:

1. A compound of the formula $$A-Ar-\underset{R^2}{\overset{R^1}{N}}-\underset{R^3}{\overset{R^3}{\underset{|}{C}}}-\underset{R^5}{\overset{R^4}{\underset{|}{C}}}-\underset{O}{\overset{O}{C}}-\underset{H}{N}-\underset{S}{\overset{}{\underset{}{}}}\!\!\equiv\!\!\quad(I)$$

wherein:

A is a group of the formula

[structural formulas shown]

in which m is the number 1 or 2, $R^{8a}$ is in each case independently of one another a hydrogen atom or a $C_{1-3}$-alkyl, hydroxy, hydroxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$- alkyl)-amino-$C_{1-3}$-alkyl group, where in the aforementioned substituted 5- to 7-membered groups A, the heteroatoms O or N which may optionally be introduced as substituents with $R^{8a}$, are not separated by exactly one carbon atom from a heteroatom from the group of N, O, S, $R^{8b}$ is in each case independently of one another a hydrogen atom or a $C_{1-3}$-alkyl group, $X^1$ is a carbonyl, C=$NR^{8c}$, C=N—$OR^{8c}$, C=N—CN or sulphonyl group, $R^{8c}$ is in each case independently of one another a hydrogen atom, a $C_{1-3}$-alkyl, $C_{1-3}$-alkylcarbonyl, or a $C_{1-4}$-alkyloxycarbonyl group, $X^2$ is an oxygen atom or an —$NR^{8b}$— group, where $R^{8b}$ is as defined above, $X^3$ is a carbonyl, C=$NR^{8c}$, C=N—$OR^{8c}$, C=N—CN or sulphonyl group, where $R^{8c}$ is as defined above, $X^4$ is an oxygen atom or an —$NR^{8c}$- group, where $R^{8c}$ is as defined above, Ar is a phenyl or pyridyl group, $R^1$ is a hydrogen, fluorine, chlorine, bromine or iodine atom, a methyl or a methoxy group, where the hydrogen atoms of the methyl or methoxy group may optionally be wholly or partly replaced by fluorine atoms, $R^2$ is a hydrogen or fluorine atom or a methyl group, $R^3$ is a hydrogen atom, $R^4$ is a $C_{2-4}$-alkenyl or $C_{2-4}$-alkynyl group,
  a straight-chain or branched $C_{1-6}$-alkyl group,
    where the hydrogen atoms of the straight-chain or branched
      $C_{1-6}$-alkyl group may optionally be replaced wholly or partly by fluorine atoms, and which may optionally be substituted by a
        $C_{3-5}$-cycloalkyl group, a nitrile, hydroxy, a $C_{1-5}$-alkyloxy group, where the hydrogen atoms of the $C_{1-5}$-alkyloxy group may optionally be replaced wholly or partly by fluorine atoms, or $C_{1-5}$-alkylcarbonyloxy, $C_{1-5}$-alkyloxycarbonyloxy, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleniminocarbonyl, aminosulphonyl, $C_{1-5}$-alkylaminosulphonyl, di-($C_{1-5}$-alkyl)-aminosulphonyl, $C_{3-6}$-cycloalkyleniminosulphonyl, di-($C_{1-5}$-alkyl)-phosphoryl, amino, $C_{1-5}$-alkylamino, di-($C_{1-5}$-alkyl)-amino, $C_{1-5}$-alkylcarbonylamino, $C_{1-5}$-alkyl-sulphonylamino, or an N—($C_{1-5}$-alkylsulphonyl)-$C_{1-5}$-alkylamino group,
    a phenyl, heteroaryl, phenyl-$C_{1-3}$-alkyl or heteroaryl-$C_{1-3}$-alkyl group,
      which may optionally be substituted in the phenyl or heteroaryl moiety once to three times by identical or different substituents selected from the group consisting of halogen atoms, $C_{1-3}$-alkyl, di-($C_{1-3}$-alkyl)-amino, hydroxy, $C_{1-3}$-alkyloxy, mono-, di - and trifluoromethoxy groups, $R^5$ is a hydrogen atom or a straight-chain or branched $C_{1-4}$-alkyl group, where the hydrogen atoms of the straight-chain or branched $C_{1-4}$-alkyl group may optionally be wholly or partly replaced by fluorine atoms, or $R^4$ and $R^5$ together with the carbon atom to which they are bonded form a $C_{3-8}$-cycloalkyl group,
  where one of the methylene groups of a $C_{4-8}$-cycloalkyl group may be replaced by an oxygen or sulphur atom or a sulphonyl or
  —N($R^{8c}$)— group, where $R^{8c}$ is as defined above, and/or
  two directly adjacent methylene groups of a $C_{4-8}$-cycloalkyl group may together be replaced by a —C(O)N($R^{8b}$)— or —S(O)$_2$N($R^{8b}$)— group, where $R^{8b}$ is as defined above, and/or
  three directly adjacent methylene groups of a $C_{6-8}$-cycloalkyl group may together be replaced by a —OC(O)O—, —OC(O)N($R^{8b}$)—, —N($R^{8b}$)C(O)N($R^{8b}$)— or —N($R^{8b}$)S(O)$_2$N(R )— group, where $R^{8b}$ is as defined above,
  where 1 to 2 carbon atoms of a $C_{3-8}$-cycloalkyl group may optionally be substituted independently of one another by a $C_{1-3}$-alkyl, hydroxy, $C_{1-3}$-alkyloxy, $C_{1-3}$-alkyloxycarbonyl, $C_{1-3}$-alkylamino, di-($C_{1-3}$-alkyl)-amino group,
    with the proviso that such a $C_{3-8}$-cycloalkyl group formed together from $R^4$ and $R^5$
      in which two heteroatoms in the ring selected from the group of oxygen and nitrogen are separated from one another by exactly one optionally substituted —CH$_2$— group, and/or
      in which one or both methylene groups in the ring which are connected directly to the carbon atom to which the groups $R^4$ and $R^5$ are attached are replaced by a heteroatom from the group of oxygen, nitrogen and sulphur, and/or
      in which a substituent which is linked to the cyclic group, and which is distinguished by a heteroatom from the group of oxygen, nitrogen, sulphur and halogen atom being directly linked to the cyclic group, is separated from another heteroatom from the group of oxygen, nitrogen and sulphur, with the exception of the sulphone group, by exactly one optionally substituted methylene group, and/or
      in which two oxygen atoms are directly connected together, is excluded, where, unless otherwise mentioned, the term "heteroaryl group" mentioned above in the definitions means a monocyclic 5- or 6-membered heteroaryl group, where
  the 6-membered heteroaryl group comprises one, two or three nitrogen atoms and
  the 5-membered heteroaryl group comprises an imino group which is optionally substituted by a $C_{1-3}$-alkyl, phenyl or phenyl-$C_{1-3}$-alkyl group, or an oxygen or sulphur atom or
  an imino group which is optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkylenimino-$C_{1-3}$-alkyl or phenyl-$C_{1-3}$-alkyl group, or an oxygen or sulphur atom and additionally a nitrogen atom or
  an imino group which is optionally substituted by a $C_{1-3}$-alkyl or phenyl-$C_{1-3}$-alkyl group, and two or three nitrogen atoms,
  and additionally a phenyl ring which is optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkylenimino group may be fused to the aforementioned monocyclic heteroaryl groups via two adjacent carbon atoms,
  and the linkage takes place via a nitrogen atom or via a carbon atom of the heterocyclic moiety or of a fused phenyl ring, where, unless otherwise mentioned, the term "halogen atom" mentioned above in the definitions means an atom from the group of fluorine, chlorine, bromine and iodine, where the alkyl, alkynyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different, and where the hydrogen atoms in the methyl or ethyl groups present in the aforementioned definitions may, unless otherwise mentioned, be wholly or partly replaced by fluorine atoms, or a tautomer or salt thereof.

2. A compound of the formula I according to claim 1, wherein:

A is a group of the formula

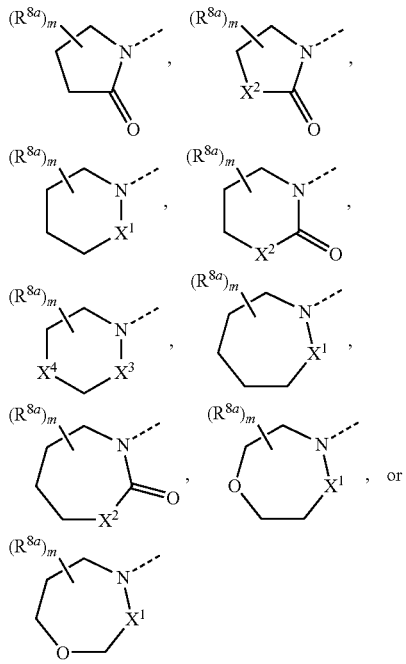

in which m is the number 1 or 2, $R^{8a}$ is in each case independently of one another a hydrogen atom or a $C_{1-3}$-alkyl group, $X^1$ is a carbonyl, C=NH, C=N—OH, C=N—CN or sulphonyl group, $X^2$ is an oxygen atom or an —$NR^{8b}$— group, $R^{8b}$ is a hydrogen atom or a $C_{1-3}$-alkyl group, $X^3$ is a carbonyl, C=NH, C=N—OH, C=N—CN or sulphonyl group, $R^{8c}$ is a hydrogen atom, a $C_{1-3}$-alkyl, $C_{1-3}$-alkylcarbonyl, or a $C_{1-4}$-alkyloxycarbonyl group, $R^1$ is a hydrogen, fluorine, chlorine, bromine or iodine atom, a methyl or a trifluoromethyl group, $R^2$ is a hydrogen or fluorine atom, $R^4$ is a straight-chain or branched $C_{1-6}$-alkyl group, where the hydrogen atoms of the straight-chain or branched $C_{1-6}$-alkyl group may optionally be wholly or partly replaced by fluorine atoms, and which may optionally be substituted by a hydroxy, a $C_{1-5}$-alkyloxy group, $C_{1-5}$-alkylsulphanyl, $C_{1-5}$-allylsulphinyl, $C_{1-5}$-alkylsulphonyl, carboxy, $C_{1-5}$-alkyloxycarbonyl, di-($C_{1-5}$-alkyl)-phosphoryl group, a phenyl, phenyl-$C_{1-2}$-alkyl, heteroaryl-$C_{1-2}$-alkyl or C-linked heteroaryl group, where the heteroaryl group is selected from the group consisting of imidazolyl, furanyl, pyrazolyl, tetrazolyl and pyridinyl, and which may optionally be substituted in the phenyl or heteroaryl moiety once to twice by identical or different substituents selected from chlorine or fluorine atoms or $C_{1-3}$-alkyl groups, $R^5$ is a hydrogen atom or a straight-chain or branched $C_{1-4}$-alkyl group, where the hydrogen atoms of the straight-chain or branched $C_{1-4}$-alkyl group may optionally be replaced wholly or partly by fluorine atoms, or $R^4$ and $R^5$ together with the carbon atom to which they are bonded form a $C_{3-7}$-cycloalkyl group, where one of the methylene groups of a $C_{4-8}$-cycloalkyl group may be replaced by an oxygen or sulphur atom or a sulphonyl or —$N(R^{8c})$— group, where $R^{8c}$ is as defined above, and/or two directly adjacent methylene groups of a $C_{4-8}$-cycloalkyl group may together be replaced by a —C(O)N($R^{8b}$)— or —S(O)$_2$N(R )— group, where $R^{8b}$ is as defined above, and/or three directly adjacent methylene groups of a $C_{6-8}$-cycloalkyl group may together be replaced by a —OC(O)O—, —OC(O)N($R^{8b}$)—, —N($R^{8b}$)C(O)N($R^{8b}$)— or —N($R^{8b}$)S(O)$_2$N($R^{8b}$)— group, where $R^{8b}$ is as defined above, where 1 to 2 carbon atoms of a $C_{3-7}$-cycloalkyl group may optionally be substituted independently of one another by a $C_{1-3}$-alkyl, hydroxy, $C_{1-3}$-alkyloxy or di-($C_{1-3}$-alkyl)-amino group, with the proviso that such a $C_{3-7}$-cycloalkyl group formed together from $R^4$ and $R^5$, in which two heteroatoms in the ring selected from the group of oxygen and nitrogen are separated from one another by exactly one optionally substituted —$CH_2$— group, and/or in which one or both methylene groups of the ring which are directly connected to the carbon atom to which the groups $R^4$ and $R^5$ are attached are replaced by a heteroatom from the group of oxygen, nitrogen and sulphur, and/or in which a substituent which is linked to the cyclic group, and which is distinguished in that an oxygen or nitrogen atom is directly linked to the cyclic group, is separated from another heteroatom from the group of oxygen, nitrogen and sulphur, with the exception of the sulphone group, by exactly one, optionally substituted methylene group, and/or in which two oxygen atoms are directly connected together, is excluded, where, unless mentioned otherwise, the term "halogen atom" mentioned above in the definitions means an atom from the group of fluorine, chlorine, bromine and iodine, where the alkyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different, and where the hydrogen atoms in the methyl or ethyl groups present in the aforementioned definitions may, unless otherwise mentioned, be wholly or partly replaced by fluorine atoms, or a tautomer or salt thereof.

3. A compound of the formula I according to claim 1, wherein:

A is a group of the formula

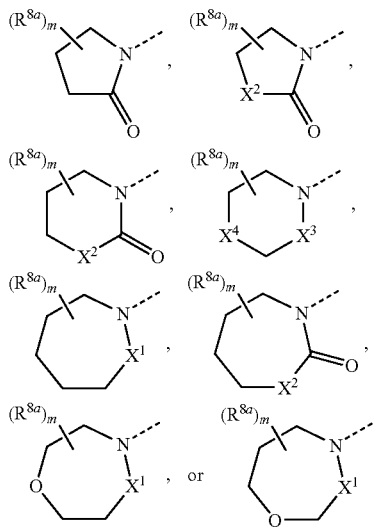

in which m is the number 1 or 2, $R^{8a}$ is in each case independently of one another a hydrogen atom or a $C_{1-3}$-alkyl group, $X^1$ is a carbonyl, C=NH, C=N—OH, C=N—CN or suiphonyl group, $X^2$ is an oxygen atom or an —$NR^{8b}$— group, $R^{8b}$ is a hydrogen atom or a $C_{1-3}$-alkyl group, $X^3$ is a carbonyl, C=NH, C=N—OH, C=N—CN or suiphonyl group, $R^{8c}$ is a hydrogen atom, a $C_{1-3}$-alkyl, $C_{1-3}$-alkylcarbonyl, or a $C_{1-4}$-alkyloxycarbonyl group, $R^1$ is a hydrogen, chlorine or bromine atom, a methyl or trifluoromethyl group, $R^2$ is a hydrogen or fluorine atom, $R^4$ is a trifluoromethyl group, a straight-chain or branched $C_{1-4}$-alkyl group which may optionally be substituted by a hydroxy, a $C_{1-5}$-alkyloxy group, $C_{1-5}$-alkylsulphanyl, $C_{1-5}$-allylsulphinyl, $C_{1-5}$-alkylsulphonyl, carboxy, $C_{1-5}$-alkyloxycarbonyl, di-($C_{1-5}$-alkyl)-phosphoryl group, a phenyl, benzyl, heteroaryl-$C_{1-2}$-alkyl or C-linked heteroaryl group, where the heteroaryl group is selected from the group consisting of imidazolyl, furanyl, pyrazolyl, tetrazolyl and pyridinyl, and which may optionally be substituted in the phenyl or heteroaryl moiety once to twice by identical or different substituents selected from chlorine or fluorine atoms or $C_{1-3}$-alkyl groups, $R^5$ is a hydrogen atom or a methyl group, or $R^4$ and $R^5$ together with the carbon atom to which they are bonded form a $C_{3-6}$-cycloalkyl group, where one of the methylene groups of a $C_{4-6}$-cycloalkyl group may be replaced by an oxygen or sulphur atom or an —N($R^{8c}$)— group, where $R^{8c}$ is as defined above, with the proviso that such a $C_{3-6}$-cycloalkyl group formed together from $R^4$ and $R^5$, in which one or both methylene groups of the ring which is directly connected to the carbon atom to which the groups $R_4$ and $R_5$ are attached are replaced by a heteroatom from the group of oxygen, nitrogen and sulphur, is excluded where, unless mentioned otherwise, the term "halogen atom" mentioned above in the definitions means an atom from the group of fluorine, chlorine, bromine and iodine, where the alkyl and alkoxy groups which are present in the aforementioned definitions and which have more than two carbon atoms may, unless otherwise mentioned, be straight-chain or branched, and the alkyl groups in the aforementioned dialkylated groups, for example the dialkylamino groups, may be identical or different, and where the hydrogen atoms in the methyl or ethyl groups present in the aforementioned definitions may, unless otherwise mentioned, be wholly or partly replaced by fluorine atoms, or a tautomer or salt thereof.

4. A compound of the formula I according to claim 1, wherein:

A is a group of the formula

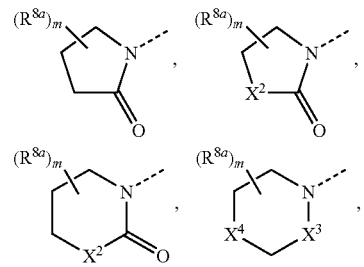

in which m is the number 1 or 2, $R^{8a}$ is in each case independently of one another a hydrogen atom or a $C_{1-3}$-alkyl group, $X^1$ is a carbonyl group, $X^2$ is an oxygen atom or an —$NR^{8b}$— group, $R^{8b}$ is a hydrogen atom or a $C_{1-3}$-alkyl group, $X^3$ is a carbonyl group, $R^{8c}$ is a hydrogen atom or a $C_{13}$-alkyl group, $R^1$ is a hydrogen, chlorine or bromine atom, a methyl or trifluoromethyl group, $R^2$ is a hydrogen atom, $R^4$ is a straight-chain or branched $C_{1-4}$-alkyl group, which may optionally be substituted by a hydroxy, a $C_{1-5}$-alkyloxy group, $C_{1-5}$-alkylsulphanyl, $C_{1-5}$-allylsulphinyl, $C_{1-5}$-alkylsulphonyl, carboxy, $C_{1-5}$-alkyloxycarbonyl, di-($C_{1-5}$-alkyl)-phosphoryl group, a heteroaryl-$C_{1-2}$-alkyl or C-linked heteroaryl group, where the heteroaryl group is selected from the group consisting of imidazolyl, furanyl, pyrazolyl, tetrazolyl and pyridinyl, $R^5$ is a hydrogen atom or a methyl group, or $R^4$ and $R^5$ together with the carbon atom to which they are bonded form a $C_{3-6}$-cycloalkyl group, where one of the methylene groups of a $C_{4-6}$-cycloalkyl group may be replaced by an oxygen or sulphur atom or an —N($R^{8c}$)— group, where $R^{8c}$ is as defined above, with the proviso that such a $C_{3-6}$-cycloalkyl group formed together from $R^4$ and $R^5$,
in which one or both methylene groups of the ring which are directly connected to the carbon atom to which the groups $R^4$ and $R^5$ are attached are replaced by a heteroatom from the group of oxygen, nitrogen and sulphur, is excluded, where the alkyl and alkoxy groups which are present in the aforementioned definitions and which comprise more than two carbon atoms can, unless mentioned otherwise, be straight-chain or branched, and the alkyl groups in the aforementioned dialkylated groups, for example the dialkylamino groups, may be identical or different, and where the hydrogen atoms of the methyl or ethyl groups present in the aforementioned definitions may, unless mentioned otherwise, be replaced wholly or partly by fluorine atoms, or a tautomer or salt thereof.

5. A compound of the formula I according to claim 1, wherein the group A and the —N(R³)—C(O)—C(R⁴R⁵)—NH—CO— chain are disposed in the 1,4 position relative to one another.

6. A compound of the formula I according to claim 1, wherein the group A is the group

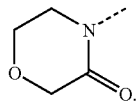

7. A compound of the formula I according to claim 1, wherein neither $R^4$ nor $R^5$ is hydrogen.

8. A compound of the formula I according to claim 1, wherein $R^4$ and $R^5$ together with the carbon atom to which they are bonded form a cyclic group.

9. A compound of the formula I according to claim 8, wherein $R^4$ and $R^5$ together with the carbon atom to which they are bonded form a cyclic group, which is a $C_{3-8}$-cycloalkyl group, a $C_{3-7}$-cycloalkyl group or a $C_{3-6}$-cycloalkyl group.

10. A compound selected from the group consisting of:
5-ethynyl-N-{1-methyl-1-[3-methyl-4-(3-oxomorpholin-4-yl)phenylcarbamoyl]ethyl}thiophene-2-carboxamide,
5-ethynyl-N-{3-[3-methyl-4-(3-oxomorpholin-4-yl)phenylcarbamoyl]tetrahydrofuran-3-yl}thiophene-2-carboxamide,
5-ethynyl-N-{2-methoxy-1-[3-methyl-4-(3-oxomorpholin-4-yl) phenylcarbamoyl]ethyl}thiophene-2-carboxamide,
5-ethynyl-N-{1-methyl-1-[3-trifluoromethyl-4-(3-oxomorpholin-4-yl) phenylcarbamoyl]ethyl}thiophene-2-carboxamide,
5-ethynyl-N-{1-methyl-1-[3-bromo-4-(3-oxomorpholin-4-yl)phenylcarbamoyl]ethyl}thiophene-2-carboxamide,
5-ethynyl-N-{1-[3-methyl-4-(3-oxomorpholin-4-yl)phenylcarbamoyl]ethyl}thiophene-2-carboxamide,
5-ethynyl-N-{1-[3-methyl-4-(3-oxomorpholin-4-yl)phenylcarbamoyl]butyl}thiophene-2-carboxamide,
5-ethynyl-N-{2-methoxy-1-[3-methyl-4-(3-oxomorpholin-4-yl) phenylcarbamoyl]propyl}thiophene-2-carboxamide,
5-ethynyl-N-{2-methylsulphanyl-1-[3-methyl-4-(3-oxomorpholin-4-yl) phenylcarbamoyl]ethyl}thiophene-2-carboxamide,
5-ethynyl-N-{2-methylsulphinyl-1-[3-methyl-4-(3-oxomorpholin-4-yl) phenylcarbamoyl]ethyl}thiophene-2-carboxamide,
5-ethynyl-N-{2-methylsulphonyl-1-[3-methyl-4-(3-oxomorpholin-4-yl) phenylcarbamoyl]ethyl}thiophene-2-carboxamide,
5-ethynyl-N-{3-methylsulphanyl-1-[3-methyl-4-(3-oxomorpholin-4-yl) phenylcarbamoyl]propyl}thiophene-2-carboxamide,
5-ethynyl-N-{3-methylsulphinyl-1-[3-methyl-4-(3-oxomorpholin-4-yl) phenylcarbamoyl]propyl}thiophene-2-carboxamide,
5-ethynyl-N-{3-methylsulphonyl-1-[3-methyl-4-(3-oxomorpholin-4-yl) phenylcarbamoyl]propyl}thiophene-2-carboxamide,
5-ethynyl-N-{2-dimethoxyphosphoryl-1-[3-methyl-4-(3-oxomorpholin-4-yl) phenylcarbamoyl]ethyl}thiophene-2-carboxamide,
5-ethynyl-N-{3-methoxycarbonyl-1-[3-methyl-4-(3-oxomorpholin-4-yl) phenylcarbamoyl]propyl}thiophene-2-carboxamide,
5-ethynyl-N-{3-hydroxycarbonyl-1-[3-methyl-4-(3-oxomorpholin-4-yl) phenylcarbamoyl]propyl}thiophene-2-carboxamide,
5-ethynyl-N-{3-(tetrazol-5-yl)-1-[3-methyl-4-(3-oxomorpholin-4-yl) phenylcarbamoyl]propyl}thiophene-2-carboxamide,
5-ethynyl-N-{2-phenyl-1-[3-methyl-4-(3-oxomorpholin-4-yl)phenylcarbamoyl]ethyl}thiophene-2-carboxamide,
5-ethynyl-N-{2-(pyridin-3-yl)-1-[3-methyl-4-(3-oxomorpholin-4-yl) phenylcarbamoyl]ethyl}thiophene-2-carboxamide,
5-ethynyl-N-{1-(pyridin-3-yl)-1-[3-methyl-4-(3-oxomorpholin-4-yl) phenylcarbamoyl]methyl}thiophene-2-carboxamide,
5-ethynyl-N-{1-(1H-imidazol-4-yl)-1-[3-methyl-4-(3-oxomorpholin-4-yl) phenylcarbamoyl]methyl}thiophene-2-carboxamide,
5-ethynyl-N-{1-(1H-1-methylimidazol-4-yl)-1-[3-methyl-4-(3-oxomorpholin-4-yl) phenylcarbamoyl]methyl}thiophene-2-carboxamide,
5-ethynyl-N-{1-(1H-1-methylpyrazol-3-yl)-1-[3-methyl-4-(3-oxomorpholin-4-yl) phenylcarbamoyl]methyl}thiophene-2-carboxamide,
5-ethynyl-N-{1-(furan-2-yl)-1-[3-methyl-4-(3-oxomorpholin-4-yl) phenylcarbamoyl]methyl}thiophene-2-carboxamide,
5-ethynyl-N-{1-methoxymethyl-1-[3-methyl-4-(3-oxomorpholin-4-yl) phenylcarbamoyl]ethyl}thiophene-2-carboxamide,
5-ethynyl-N-{1-methylsulphanylmethyl-1-[3-methyl-4-(3-oxomorpholin-4-yl) phenylcarbamoyl]ethyl}thiophene-2-carboxamide,
5-ethynyl-N-{1-trifluoromethyl-1-[3-methyl-4-(3-oxomorpholin-4-yl) phenylcarbamoyl]ethyl}thiophene-2-carboxamide,
5-ethynyl-N-{1-methyl-1-[6-fluoro-3-methyl-4-(3-oxomorpholin-4-yl) phenylcarbamoyl]ethyl}thiophene-2-carboxamide,
5-ethynyl-N-{1-[3-methyl-4-(3-oxomorpholin-4-yl)phenylcarbamoyl]cyclobut-1-yl}thiophene-2-carboxamide, 5-ethynyl-N-{1-[3-methyl-4-(3-oxomorpholin-4-yl)phenylcarbamoyl]cyclopent-1-yl}thiophene-2-carboxamide, 5-ethynyl-N-{1-[3-methyl-4-(3-oxomorpholin-4-yl)phenylcarbamoyl]cyclohex-1-yl}thiophene-2-carboxamide, 5-ethynyl-N-{3-[4-(3-oxomorpholin-4-yl)phenylcarbamoyl]tetrahydrofuran-3-yl}thiophene-2-carboxamide, 5-ethynyl-N-{3-[3-bromo-4-(3-oxomorpholin-4-yl)phenylcarbamoyl]tetrahydrofuran-3-yl}thiophene-2-carboxamide, 5-ethynyl-N-{3-[3-methyl-4-(3-oxomorpholin-4-yl)phenylcarbamoyl]oxetan-3-yl}thiophene-2-carboxamide, 5-ethynyl-N-{3-[3-methyl-4-(3-oxomorpholin-4-yl)phenylcarbamoyl]thietan-3-yl}thiophene-2-carboxamide, 5-ethynyl-N-{3-[3-methyl-4-(3-oxomorpholin-4-yl)phenylcarbamoyl]-1,1-dioxothietan-3-yl}thiophene-2-carboxamide, 5-ethynyl-N-{5-[3-methyl-4-(3-oxomorpholin-4-yl)phenylcarbamoyl]-2-oxo-1,3-dioxinane-5-yl}thiophene-2-carboxamide, 5-ethynyl-N-{5-[3-methyl-4-(3-oxomorpholin-4-yl)phenylcarbamoyl]-2-oxohexahydropyrimidin-5-yl}thiophene-2-carboxamide, 5-ethynyl-N-{3-[3-methyl-4-(3-oxomorpholin-4-yl)phenylcarbamoyl]-5-oxopyrrolidin-3-yl}thiophene-2-carboxamide, 5-ethynyl-N-{1-methyl-3-[3-methyl-4-(3-oxomorpholin-4-yl)phenylcarbamoyl]-5-oxopyrrolidin-3-yl}thiophene-2-carboxamide, 5-ethynyl-N-{3-[3-methyl-4-(3-oxomorpholin-4-yl)phenylcarbamoyl]pyrrolidin-3-yl}thiophene-2-carboxamide, 5-ethynyl-N-{1-methyl-3-[3-methyl-4-(3-oxomorpholin-4-yl)phenylcarbamoyl]pyrrolidin-3-yl}thiophene-2-carboxamide, 5-ethynyl-N-{1-acetyl-3-[3-methyl-4-(3-oxomorpholin-4-yl)phenylcarbamoyl]pyrrolidin-3-yl}thiophene-2-carboxamide, 5-ethynyl-N-{3-[3-methyl-4-(3-oxomorpholin-4-yl)phenylcarbamoyl]acetidin-3-yl}thiophene-2-carboxamide, 5-ethynyl-N-{3-[5-(3-oxomorpholin-4-yl)pyridyl-2-carbamoyl]tetrahydrofuran-3-yl}thiophene-2-carboxamide, 5-ethynyl-N-{3-[3-methyl-4-(2-oxopyrrolidin-1-yl)phenylcarbamoyl]tetrahydrofuran-3-yl}thiophene-2-carboxamide, 5-ethynyl-N-{3-[3-methyl-4-(2-oxo-5-methylpyrrolidin-1-yl)phenylcarbamoyl]tetrahydrofuran-3-yl}thiophene-2-carboxamide, 5-ethynyl-N-{3-[3-methyl-4-(2-oxo-4-methyloxazolidin-3-yl)phenylcarbamoyl]tetrahydrofuran-3-yl}thiophene-2-carboxamide, 5-ethynyl-N-{3-[3-methyl-4-(2-oxo-4,4-dimethyloxazolidin-3-yl)phenylcarbamoyl]tetrahydrofuran-3-yl}thiophene-2-carboxamide, 5-ethynyl-N-{3-[3-methyl-4-(2-oxo-5,5-dimethylpyrrolidin-1-yl)phenylcarbamoyl]tetrahydrofuran-3-yl}thiophene-2-carboxamide, 5-ethynyl-N-{3-[3-methyl-4-(2-oxooxazolidin-3-yl)phenylcarbamoyl]tetrahydrofuran-3-yl}thiophene-2-carboxamide, 5-ethynyl-N-{3-[3-methyl-4-(2-oxoimidazolidin-1-yl)phenylcarbamoyl]tetrahydrofuran-3-yl}thiophene-2-carboxamide, 5-ethynyl-N-{3-[3-methyl-4-(3-methyl-2-oxoimidazolidin-1-yl)phenylcarbamoyl]tetrahydrofuran-3-yl}thiophene-2-carboxamide, 5-ethynyl-N-{1-methyl-1-[3-methyl-4-(2-oxopiperidin-1-yl)phenylcarbamoyl]ethyl}thiophene-2-carboxamide, 5-ethynyl-N-{1-methyl-1-[3-methyl-4-(2-oxoperhydro-1,3-oxazin-3-yl)phenylcarbamoyl]ethyl}thiophene-2-carboxamide, 5-ethynyl-N-{1-methyl-1-[3-methyl-4-(2-oxotetrahydropyrimidin-1-yl)phenylcarbamoyl]ethyl}thiophene-2-carboxamide, 5-ethynyl-N-{1-methyl-1-[3-methyl-4-(2-oxopiperazin-1-yl)phenylcarbamoyl]ethyl}thiophene-2-carboxamide, 5-ethynyl-N-{1-methyl-1-[3-methyl-4-(2-oxo-4-methylpiperazin-1-yl)phenylcarbamoyl]ethyl}thiophene-2-carboxamide, 5-ethynyl-N-{1-methyl-1-[3-methyl-4-(1,1-dioxoperhydro-1,2-thiazin-2-yl)phenylcarbamoyl]ethyl}thiophene-2-carboxamide, 5-ethynyl-N-{1-methyl-1-[3-methyl-4-(2-iminopiperidin-1-yl)phenylcarbamoyl]ethyl}thiophene-2-carboxamide, 5-ethynyl-N-{1-methyl-1-[3-methyl-4-(3-iminomorpholin-4-yl)phenylcarbamoyl]ethyl}thiophene-2-carboxamide, 5-ethynyl-N-{1-methyl-1-[3-methyl-4-(2-iminoperhydroazepin-1-yl)phenylcarbamoyl]ethyl}thiophene-2-carboxamide, 5-ethynyl-N-{1-methyl-1-[3-methyl-4-(5-oxoperhydro-1,4-oxazepin-4-yl)phenylcarbamoyl]ethyl}thiophene-2-carboxamide, 5-ethynyl-N-{1-methyl-1-[3-methyl-4-(2-oxoperhydro-1,3-oxazepin-3-yl)phenylcarbamoyl]ethyl}thiophene-2-carboxamide, 5-ethynyl-N-{1-[3-chloro-4-(5-cyaniminoperhydro-1,4-oxazepin-4-yl)phenylcarbamoyl]ethyl}thiophene-2-carboxamide, and 5-ethynyl-N-{1-[3-methyl-4-(5-hydroxyiminoperhydro-1,4-oxazepin-4-yl)phenylcarbamoyl]ethyl}thiophene-2-carboxamide, or a tautomer or salt thereof.

11. A physiologically acceptable salt of a compound according to claims 1, 2, 3, 4, 5, 6, 7, 8, 9 or 10.

12. A pharmaceutical composition comprising a compound according to claim 1 and one or more inert carriers and/or diluents.

* * * * *